United States Patent
Nakatsugawa et al.

(10) Patent No.: US 9,925,393 B2
(45) Date of Patent: Mar. 27, 2018

(54) METHOD AND APPARATUS FOR DETERMINING TREATMENT REGION AND MITIGATING RADIATION TOXICITY

(71) Applicants: KABUSHIKI KAISHA TOSHIBA, Minato-ku (JP); TOSHIBA MEDICAL SYSTEMS CORPORATION, Otawara-shi (JP); THE JOHNS HOPKINS UNIVERSITY, Baltimore, MD (US)

(72) Inventors: Minoru Nakatsugawa, New York, NY (US); John Wayne Haller, Vernon Hills, IL (US); Robert Andrew Davey, Edinburgh (GB); Rachel-Louise Kvertus Koktava, Edinburgh (GB); Kosuke Sakaue, Otawara (JP); Todd McNutt, Baltimore, MD (US); Harry Quon, Baltimore, MD (US); Scott Patrick Robertson, Baltimore, MD (US); Zhi Cheng, Baltimore, MD (US)

(73) Assignees: KABUSHIKI KAISHA TOSHIBA, Minato-ku (JP); TOSHIBA MEDICAL SYSTEMS CORPORATION, Otawara-shi (JP); The Johns Hopkins University, Baltimore, MD (US)

( * ) Notice: Subject to any disclaimer, the term of this patent is extended or adjusted under 35 U.S.C. 154(b) by 187 days.

(21) Appl. No.: 15/069,688

(22) Filed: Mar. 14, 2016

(65) Prior Publication Data
US 2017/0259083 A1 Sep. 14, 2017

(51) Int. Cl.
*A61B 5/103* (2006.01)
*G06T 11/00* (2006.01)
(Continued)

(52) U.S. Cl.
CPC ............ *A61N 5/1039* (2013.01); *A61B 6/032* (2013.01); *A61B 6/06* (2013.01); *A61B 6/461* (2013.01);
(Continued)

(58) Field of Classification Search
CPC ........... A61B 6/032; A61B 6/06; A61B 6/461; A61B 6/469; A61N 5/1039; A61N 5/1049;
(Continued)

(56) References Cited

U.S. PATENT DOCUMENTS 8,325,878 B2 12/2012 McNutt et al.
8,688,618 B2 4/2014 McNutt et al.
(Continued)

FOREIGN PATENT DOCUMENTS

WO WO 2015/081086 A1 6/2015
WO WO 2015/176011 A1 11/2015

OTHER PUBLICATIONS

Z. Cheng et.al, The Role of a Decision Tree Model to Predict Weight Loss Following Radiation Therapy in Head and Neck Cancer Patients, International Journal of Radiation Oncology, Biology, Physics, vol. 93, No. 3, Supplement, p. E335, 2015. http://www.redjournal.org/article/S0360-3016(15)02132-X/abstract.
(Continued)

*Primary Examiner* — Mark R Gaworecki
(74) *Attorney, Agent, or Firm* — Oblon, McClelland, Maier & Neustadt, L.L.P.

(57) ABSTRACT

An apparatus for determining a contour of a treatment region in a patient includes a computer processor to receive input regarding a contour of at least one organ-at-risk (OAR) adjacent to the treatment region; receive input regarding an initial contour of the treatment region; predict a radiation toxicity to the at least one OAR based on the contour of the
(Continued)

at least one OAR, the initial contour of the treatment region, and a radiation treatment regimen; determine whether the predicted radiation toxicity exceeds a threshold; and determine a contour of the treatment region by iteratively modifying the initial contour of the treatment region, and any subsequent modified contours of the treatment region, until a stopping condition is satisfied. The stopping condition can be a preselected number of iterations or that the predicted radiation toxicity using the contour in place of the initial contour is first calculated is below said threshold.

13 Claims, 19 Drawing Sheets

(51) Int. Cl.
    *A61N 5/10*     (2006.01)
    *G06T 7/00*     (2017.01)
    *A61B 6/06*     (2006.01)
    *A61B 6/00*     (2006.01)
    *A61B 6/03*     (2006.01)

(52) U.S. Cl.
CPC ............ *A61B 6/469* (2013.01); *A61N 5/1049* (2013.01); *A61N 5/1071* (2013.01); *G06T 7/0089* (2013.01); *G06T 11/008* (2013.01); *G06T 2207/10081* (2013.01); *G06T 2211/421* (2013.01); *G06T 2211/424* (2013.01)

(58) Field of Classification Search
CPC ................ A61N 5/1071; G06T 11/008; G06T 2207/10081; G06T 2211/421; G06T 2211/424
See application file for complete search history.

(56) References Cited

U.S. PATENT DOCUMENTS

| 2011/0153547 A1* | 6/2011 | McNutt ............... G06F 19/3443 706/54 |
| 2016/0310761 A1* | 10/2016 | Li ......................... A61N 5/1038 |
| 2017/0036037 A1* | 2/2017 | Luan .................... A61N 5/1031 |
| 2017/0189717 A1* | 7/2017 | MacDonald ......... A61N 5/1039 |

OTHER PUBLICATIONS

M. Nakatsugawa et.al, Prediction of Toxicity in Irradiated Head and Neck Cancer Patients Based on the Geometry of High/Middle/Low PTVs to Surrounding OARs, International Journal of Radiation Oncology, Biology, Physics, vol. 93, No. 3, Supplement, p. E368, 2015. http://www.redjournal.org/article/S0360-3016(15)02217-8/abstract.

M. Nakatsugawa et.al, Prediction of Weight Loss in Irradiated Head and Neck Cancer Patients Based on the Clinical and Dosimetric Big Data, Radiological Society of North America 2015 Scientific Assembly and Annual Meeting, MSRO25-03, 2015. https://rsna2015.rsna.org/program/details/?publicid=MSRO25-03.

* cited by examiner

| Organ at risk | Estimated dose To organ at risk | Organ at high Toxicity risk |
|---|---|---|
| Parotid gland (right) | 30 Gy | Yes |

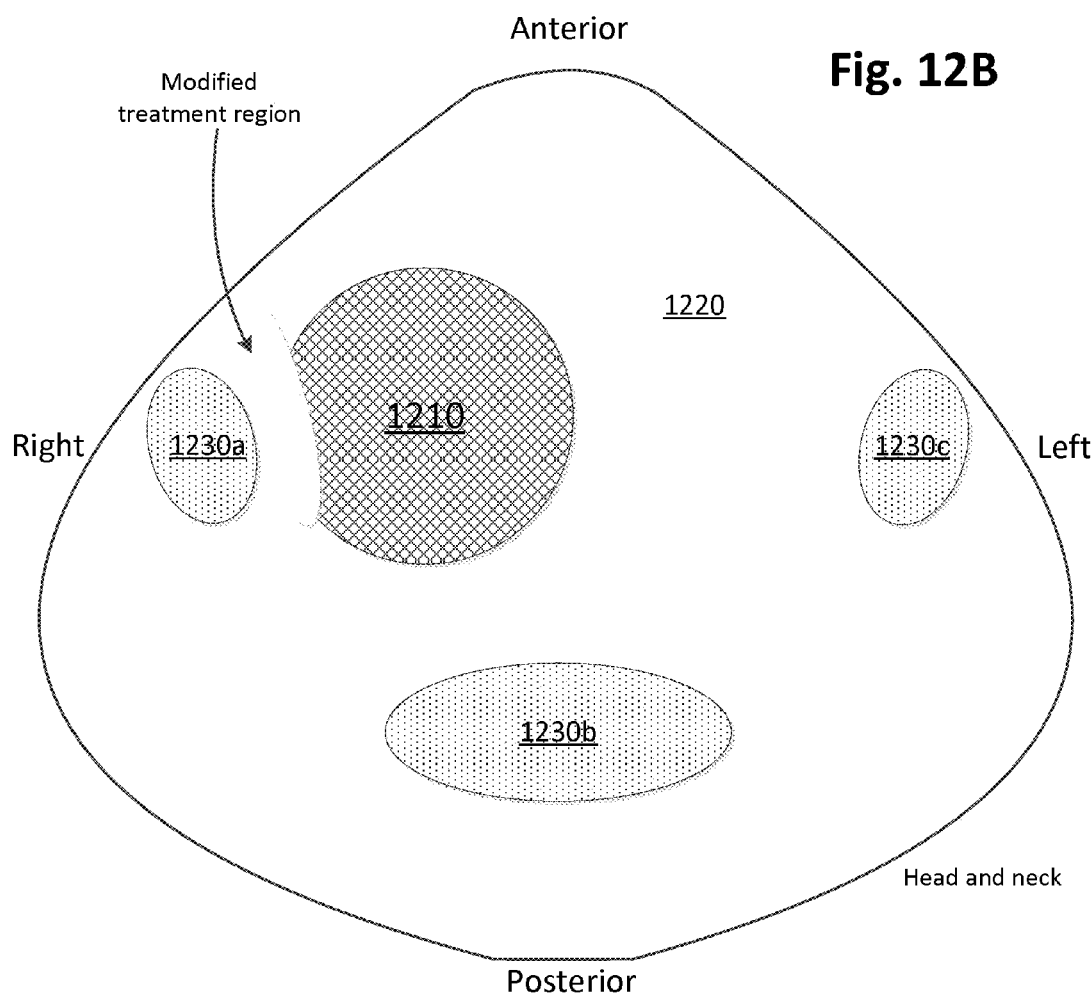

METHOD AND APPARATUS FOR DETERMINING TREATMENT REGION AND MITIGATING RADIATION TOXICITY

BACKGROUND

Radiation therapy can include X-ray therapy, gamma ray therapy, proton therapy, and heavy-ion therapy. During radiation therapy, the radiation exposure to neighboring organs can cause various side effects, referred to as "toxicity". As a result, treatment guidelines exist that determine an upper limit on an exposure dose to an organ at risk (OAR) or a region at risk, such as the National Comprehensive Cancer Network (NCCN) guidelines and the Radiation Therapy Oncology Group (RTOG) guidelines. An OAR is an organ or a region that might be damaged during exposure to radiation therapy, and usually refers to healthy organs located in the radiation field during radiation therapy, such as parotid glands, submandibular glands, and the spinal cord in the head and neck region. OARs can include any regions of interest and are not limited to organs. Treatment planning devices, such as the Philips Pinnacle, calculate a dose distribution by optimizing the radiation intensity, the number of fractions, and a radiation direction of the treatment equipment. Constraints on the prescription dosage to the treatment region exist, and a physician is also limited on the amount of radiation to neighbouring organs, which is generally less than the regulations in the guidelines.

The "background" description provided herein is for the purpose of generally presenting the context of the disclosure. Work of the presently named inventors, to the extent it is described in this background section, as well as aspects of the description which may not otherwise qualify as conventional art at the time of filing, are neither expressly nor impliedly admitted as conventional art against the present disclosure.

BRIEF DESCRIPTION OF THE DRAWINGS

A more complete understanding of the disclosure is provided by reference to the following detailed description when considered in connection with the accompanying drawings, wherein:

FIG. 12B illustrates the modified treatment region display after modification of the treatment region according to an embodiment;

DETAILED DESCRIPTION

Figure 1A:
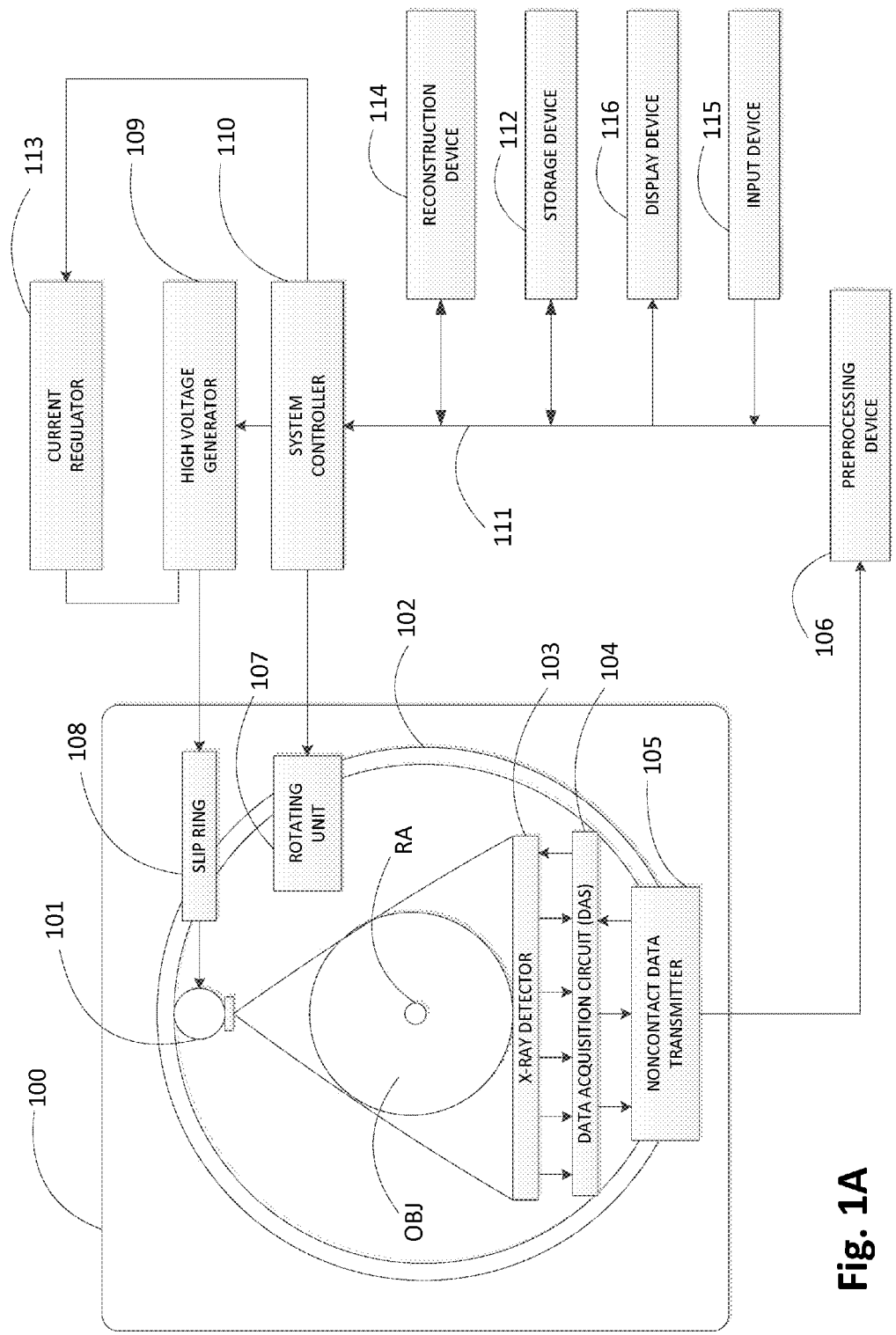
FIG. 1A is a block diagram of an exemplary CT scanner apparatus according to an embodiment.

In one embodiment, there is provided an apparatus, including a computer processor configured to (1) receive input regarding a contour of at least one organ-at-risk (OAR) adjacent to a treatment region in a patient; (2) receive input regarding an initial contour of the treatment region; (3) predict a radiation toxicity to the at least one OAR based on the contour of the at least one OAR, the initial contour of the treatment region, and a radiation treatment regimen; (4) determine whether the predicted radiation toxicity exceeds a threshold; and (5) determine a computer-generated contour of the treatment region by iteratively modifying said initial contour of the treatment region, and any subsequent modified contours of the treatment region, until a stopping condition is satisfied, wherein said stopping condition is at least one of a preselected number of iterations or that said predicted radiation toxicity using said computer-generated contour in place of said initial contour is first calculated to be below said threshold.

In another embodiment, there is provided a method, including (1) receiving input regarding a contour of at least one organ-at-risk (OAR) adjacent to a treatment region in a patient; (2) receiving input regarding an initial contour of the treatment region to receive radiation via a radiation source configured to provide the radiation to the treatment region, according to a radiation treatment regimen; (3) predicting a radiation toxicity to the at least one OAR based on the contour of the at least one OAR, the initial contour of the treatment region, and a radiation treatment regimen; (4) determining whether the predicted radiation toxicity exceeds a threshold; and (5) determining a computer-generated contour of the treatment region by iteratively modifying said initial contour of the treatment region, and any subsequent modified contours of the treatment region, until a stopping condition is satisfied, wherein said stopping condition is at least one of a preselected number of iterations or that said predicted radiation toxicity using said computer-generated contour in place of said initial contour is first calculated to be below said threshold.

In the treatment of patients with malignant tumors, a goal of radiation therapy is to deliver a high dose of radiation to the tumor volume while sparing OARs. During implementation, a patient undergoing radiation treatment is imaged by a CT/MRI/PET scanner, wherein the scan is segmented to identify the primary tumor volume and any OARs. The segmented scan is used by a dosimetrist to determine the best set of multi-leaf collimator settings to deliver a set of intensity-modulated megavoltage X-ray beams to the tumor.

One unit of measure for the amount of radiation dosage is a Gray, notated as Gy. A Gy is the absorption of one joule of radiation energy per one kilogram of matter in the International System of Units (SI). A Gy is used as a measure of absorbed dose, specific energy, and kerma (kinetic energy released per unit mass). A rad is an equivalent cgs unit to a Gy.

Constraints are in place to restrict the amount of radiation a particular organ should receive. For example, approximately 95% or more of the tumor volume should receive a dosage of at least 70 Gy, whereas no more than 60% of the parotid should receive more than 30 Gy, and no part of the spinal cord should receive more than 45 Gy. As a result, the dosimetrist needs to optimize the intensity distribution for each of a set of beams according to an objective function within the given constraints. The objective function compares tradeoffs between tumor target coverage and normal tissue sparing to find a dose distribution that maximizes the dosage to the tumor while minimizing harmful radiation to OARs.

FIG. 1A is a block diagram of an exemplary CT scanner apparatus that can be used with embodiments described herein. As shown in FIG. 1A, a radiography gantry 100 is illustrated from a side view and further includes an X-ray tube 101, an annular frame 102, and a multi-row or two-dimensional-array-type X-ray detector 103. The X-ray tube 101 and X-ray detector 103 are diametrically mounted across an object OBJ on the annular frame 102, which is rotatably supported around a rotation axis RA. A rotating unit 107 rotates the annular frame 102 at a high speed, such as 0.4 sec/rotation, while the object OBJ is being moved along the axis RA into or out of the illustrated page.

X-ray computed tomography apparatuses include various types of apparatuses. In one example, a rotate/rotate-type apparatus has an X-ray tube and X-ray detector which rotate together around an object to be examined. In a second example, a stationary/rotate-type apparatus has many detection elements which are arrayed in the form of a ring or plane, and only an X-ray tube rotates around an object to be examined. The present disclosures can be applied to either type. With reference to FIG. 1A, the rotate/rotate type is illustrated.

The multi-slice X-ray CT apparatus further includes a high voltage generator 109 that generates a tube voltage applied to the X-ray tube 101 through a slip ring 108 so that the X-ray tube 101 generates X-rays. The X-rays are emitted towards the object OBJ, whose cross-sectional area is represented by a circle. The X-ray detector 103 is located at an opposite side from the X-ray tube 101 across the object OBJ for detecting the emitted X-rays that have transmitted through the object OBJ. The X-ray detector 103 further includes individual detector elements or units.

The CT apparatus further includes other devices for processing the detected signals from X-ray detector 103. A data acquisition circuit or a Data Acquisition System (DAS) 104 converts a signal output from the X-ray detector 103 for each channel into a voltage signal, amplifies the signal, and further converts the signal into a digital signal. The X-ray detector 103 and the DAS 104 are configured to handle a predetermined total number of projections per rotation (TPPR). Examples of TPPRs include, but are not limited to 900 TPPR, 900-1800 TPPR, and 900-3600 TPPR.

The above-described data is sent to a pre-processing device 106, which is housed in a console outside the radiography gantry 100 through a non-contact data transmitter 105. The pre-processing device 106 performs certain corrections, such as sensitivity correction on the raw data. A storage device 112 stores the resultant data, which is also called projection data at a stage immediately before reconstruction processing. The storage device 112 is connected to a system controller 110 through a data/control bus 111, together with a reconstruction device 114, input device 115, and display device 116. The system controller 110 controls a current regulator 113 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 101 and the X-ray detector 103 are diametrically mounted on the annular frame 102 and are rotated around the object OBJ as the annular frame 102 is rotated about the rotation axis RA. In the fourth-generation geometry system, the detectors are fixedly placed around the patient and an X-ray tube rotates around the patient. In an alternative embodiment, the radiography gantry 100 has multiple detectors arranged on the annular frame 102, which is supported by a C-arm and a stand.

The storage device 112 can store the measurement value representative of the irradiance of the X-rays at the X-ray detector unit 103. Further, the storage device 112 can store a dedicated program for executing the CT image reconstruction methods discussed herein.

The reconstruction device 114 can execute the CT image reconstruction methods discussed herein. Further, reconstruction device 114 can execute pre-reconstruction image processing such as volume rendering processing and image difference processing as needed. The pre-reconstruction processing of the projection data performed by the pre-processing device 106 can include correcting for detector calibrations, detector nonlinearities, polar effects, noise balancing, and material decomposition.

Post-reconstruction processing performed by the reconstruction device 114 can include filtering and smoothing the image, volume rendering processing, and image difference processing as needed. The image reconstruction process can be performed using filtered back projection, iterative image reconstruction methods, or stochastic image reconstruction methods. The reconstruction device 114 can use the storage device 112 to store projection data, reconstructed images, calibration data and parameters, and computer programs, for example.

The reconstruction device 114 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the storage device 112 can be non-volatile, such as ROM, EPROM, EEPROM or FLASH memory. The storage device 112 can also be volatile, such as static or dynamic RAM. A processor, such as a microcontroller or microprocessor, and storage device 112 can be provided to manage the electronic memory, as well as the interaction between the FPGA or CPLD and the storage device 112.

Alternatively, the CPU in the reconstruction device 114 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display device 116. The display device 116 can be an LCD display, CRT display, plasma display, OLED, LED, or any other display known in the art. The storage device 112 can be a hard disk drive, CD-ROM drive, DVD drive, FLASH drive, RAM, ROM or any other electronic storage known in the art.

Figure 1B:
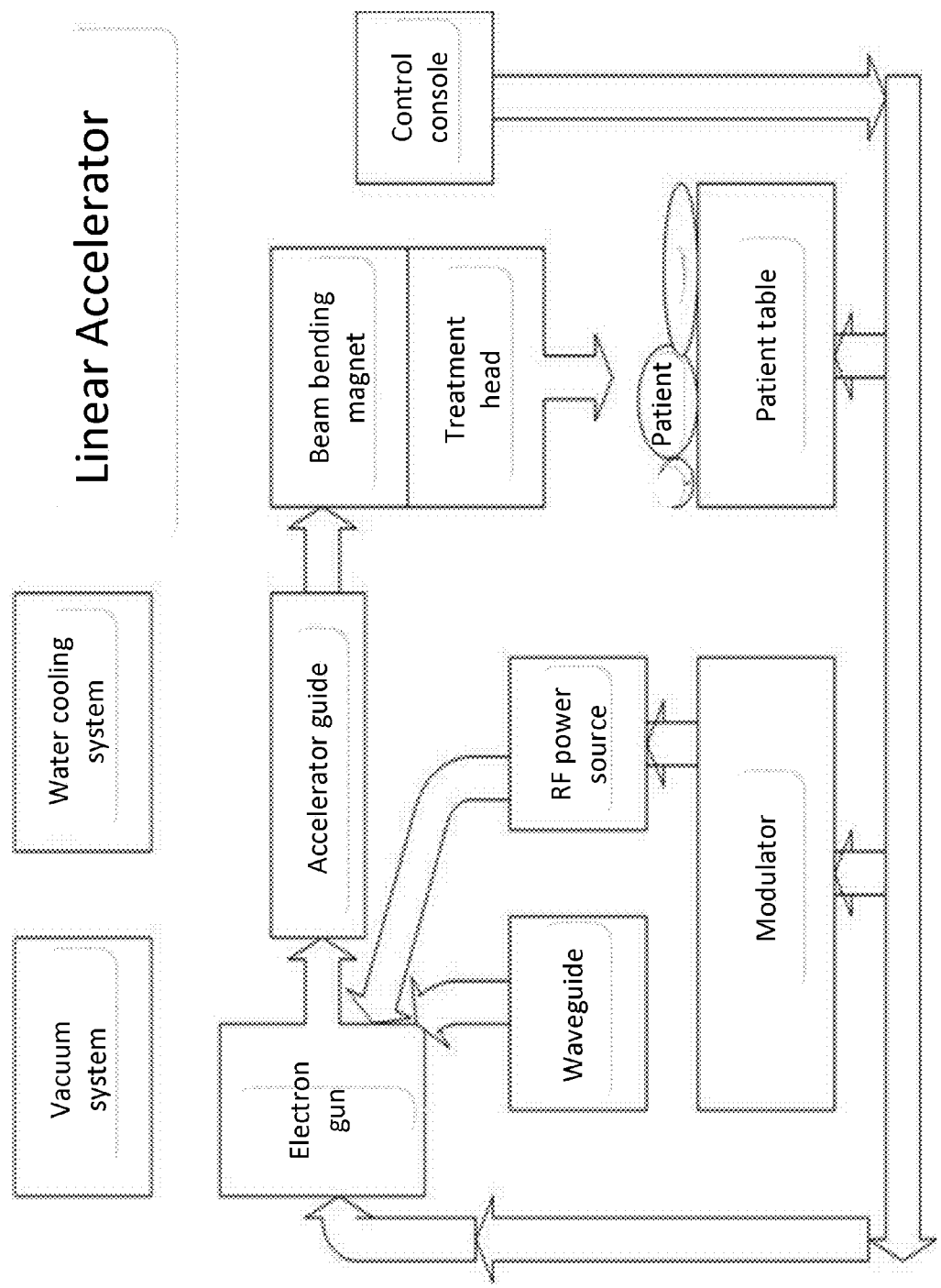
FIG. 1B is a block diagram of an exemplary linear accelerator according to an embodiment.

FIG. 1B is a block diagram of an exemplary linear accelerator (LINAC) as used with embodiments described herein. A LINAC uses electricity to form a stream of fast-moving subatomic particles to create high-energy radiation. The particles being accelerated include photons, electrons, protons, and ions.

A LINAC is an apparatus in which medical radiation treatment plans can be implemented according to embodiments described herein. Several types of external-beam radiation therapy can be implemented on a LINAC, which include, but are not limited to, three-dimensional conformal radiation therapy (3D-CRT), intensity-modulated radiation therapy (IMRT), image-guided radiation therapy (IGRT), tomotherapy, stereotactic radiosurgery (SRS), stereotactic body radiation therapy (SBRT), and proton therapy. Other charged particle beams can be used to irradiate superficial tumors, such as skin cancer or tumors near the surface of the body that do not travel very far through body tissue.

Figure 1C:
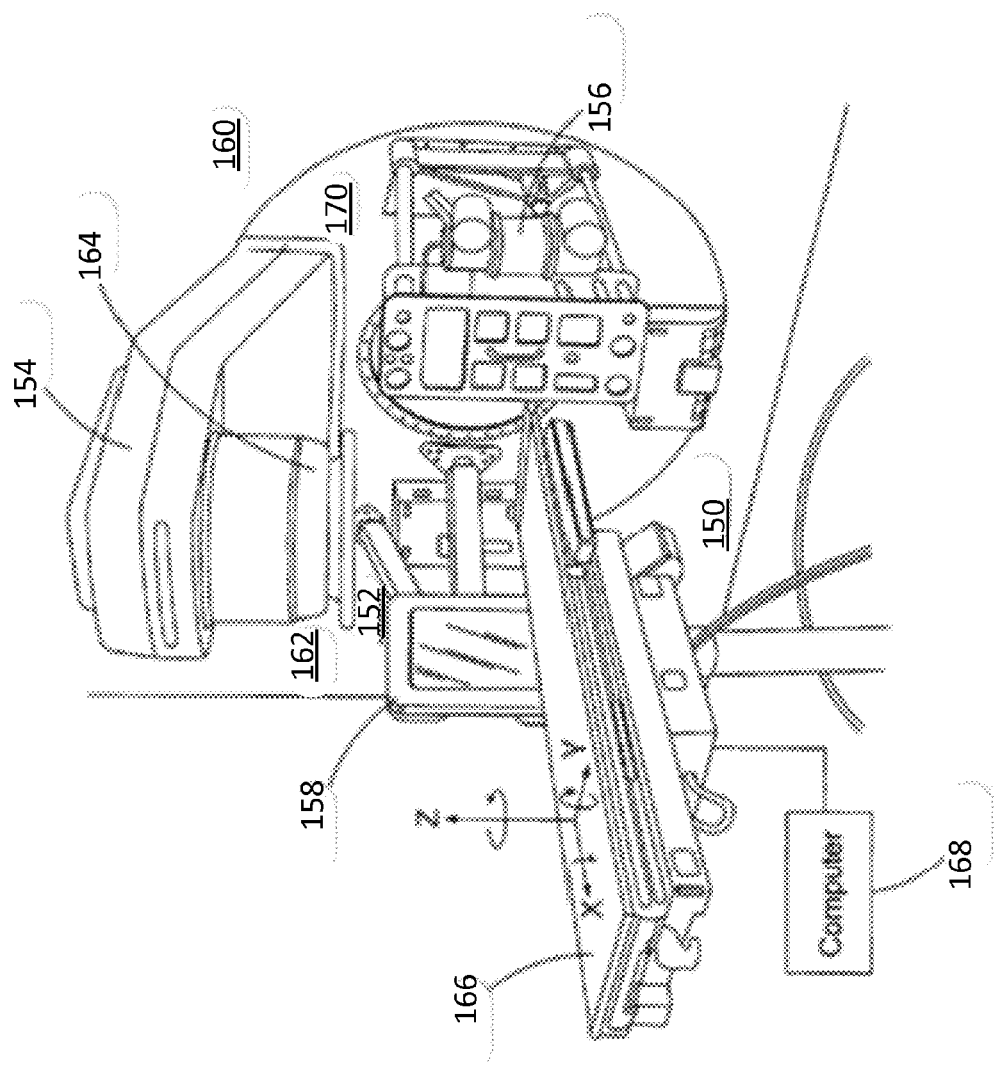
FIG. 1C is a schematic of an exemplary radiation therapy system according to an embodiment.

FIG. 1C is a schematic of an exemplary radiation therapy system 150. Radiation therapy system 150 includes an imaging system, such as a cone-beam CT system 152 and a therapeutic radiation source, such as a medical linear source or an accelerator 154. The CT system 152 includes an X-ray source 156 and a flat panel image 158 mounted on a gantry 160.

Radiation therapy system 150 is retrofitted onto a separate radiation therapy system 162, which includes a separate radiation therapy source, such as medical linear accelerator 154 that operates at a power level to allow for treatment of a target volume in an object, such as a human patient. Medical linear accelerator 154 generates a beam of X-rays or particles, such as photons, protons, or electrons that have an energy ranging from approximately 4 MeV to 25 MeV. Medical linear accelerator 154 can be replaced with other radiation sources used for therapeutic treatment of patients without departing from the scope of embodiments described herein.

Radiation therapy system 162 includes a multi-leaf collimator (MLC) 164 that includes leaves that are movable so as to define an aperture for the therapy beam to pass through towards the patient. Radiation therapy system 162 can also include an imager that is aligned with the medical linear accelerator 154 with the patient interposed there between. A computer-controlled treatment table 166 is provided for support of a patient. The treatment table 166 is controlled by a computer 168. During rotation of the treatment table 166, a ring 170 of the gantry 160 can rotate simultaneously.

When designing a radiation treatment plan, it is useful to define a shape metric that captures not only the geometries of the primary tumor volume and OARs, but also captures their configurations relative to each other. For each OAR, the distribution of the organ's volume relative to the primary tumor volume can be found. A shape signature between the tumor and OARs is used to assist in finding treatment plans utilized in similar patients. Similar treatment plans and associated side effects, such as toxicities can be reviewed and used as additional dosimetry information to determine a treatment plan.

A relationship exists between the region of radiation treatment and certain side effects. Side effects can be reduced by modifying the contour of the region of radiation treatment. However, it can take several days for medical dosimetrists to create a treatment plan, which includes an intensity of dosage, the number of fractions, and direction and distribution of the radiation dosage. When a region of radiation treatment has been specified, repeating an optimization calculation by changing the constraints of computation is time intensive. Thus, many of the calculations are conducted by manual trial and error. Therefore, it is difficult to change a region of radiation treatment after the treatment plan has been established.

Embodiments described herein provide real-time decision support for modification of the contour of the treatment region at the time of determining the radiation treatment region and treatment plan. Determining the radiation treatment region includes predicting side effects of the radiation treatment using the radiation dose distribution of prior patients' treatment plans having treatment regions similar to the new patient.

Figure 2A:
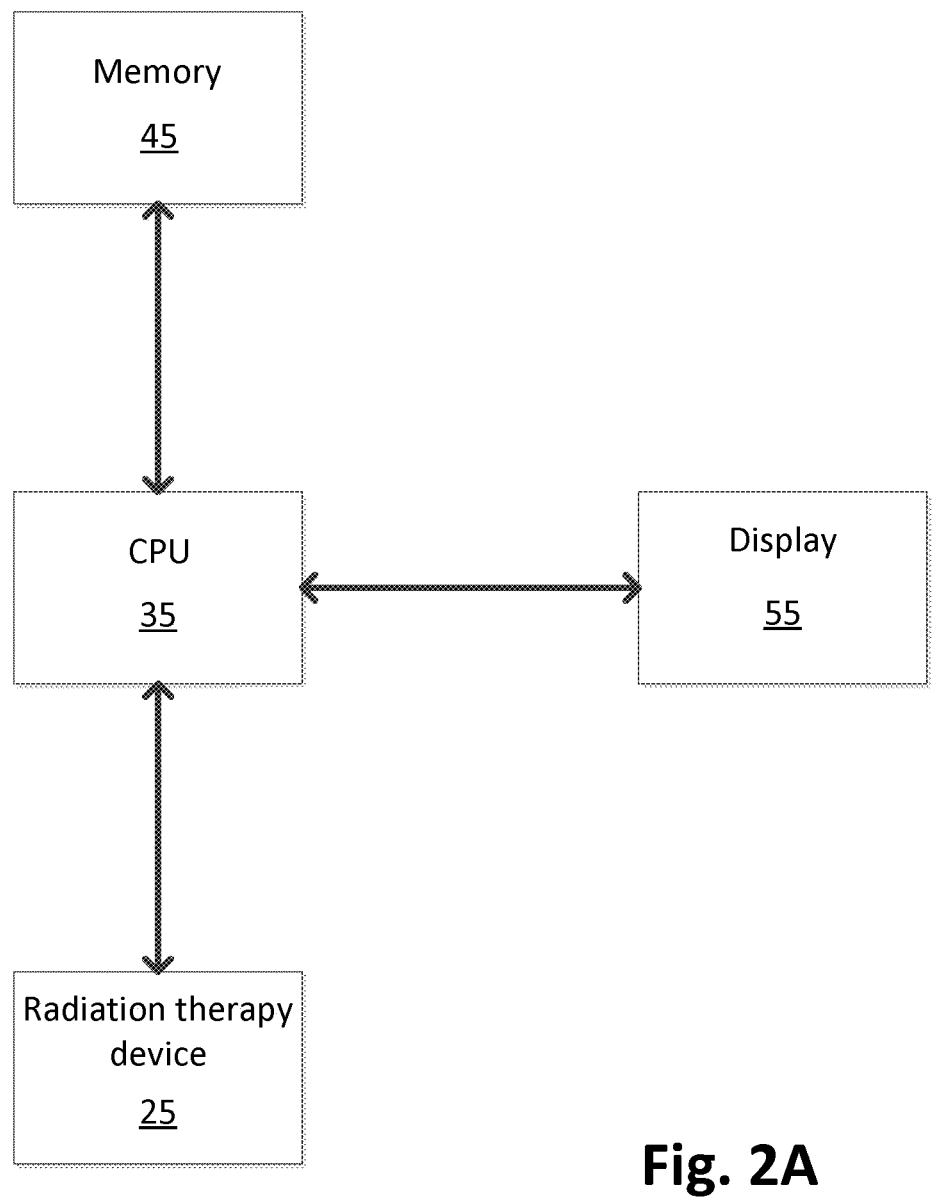
FIG. 2A is a block diagram illustrating an exemplary structure according to an embodiment.
Figure 2B:
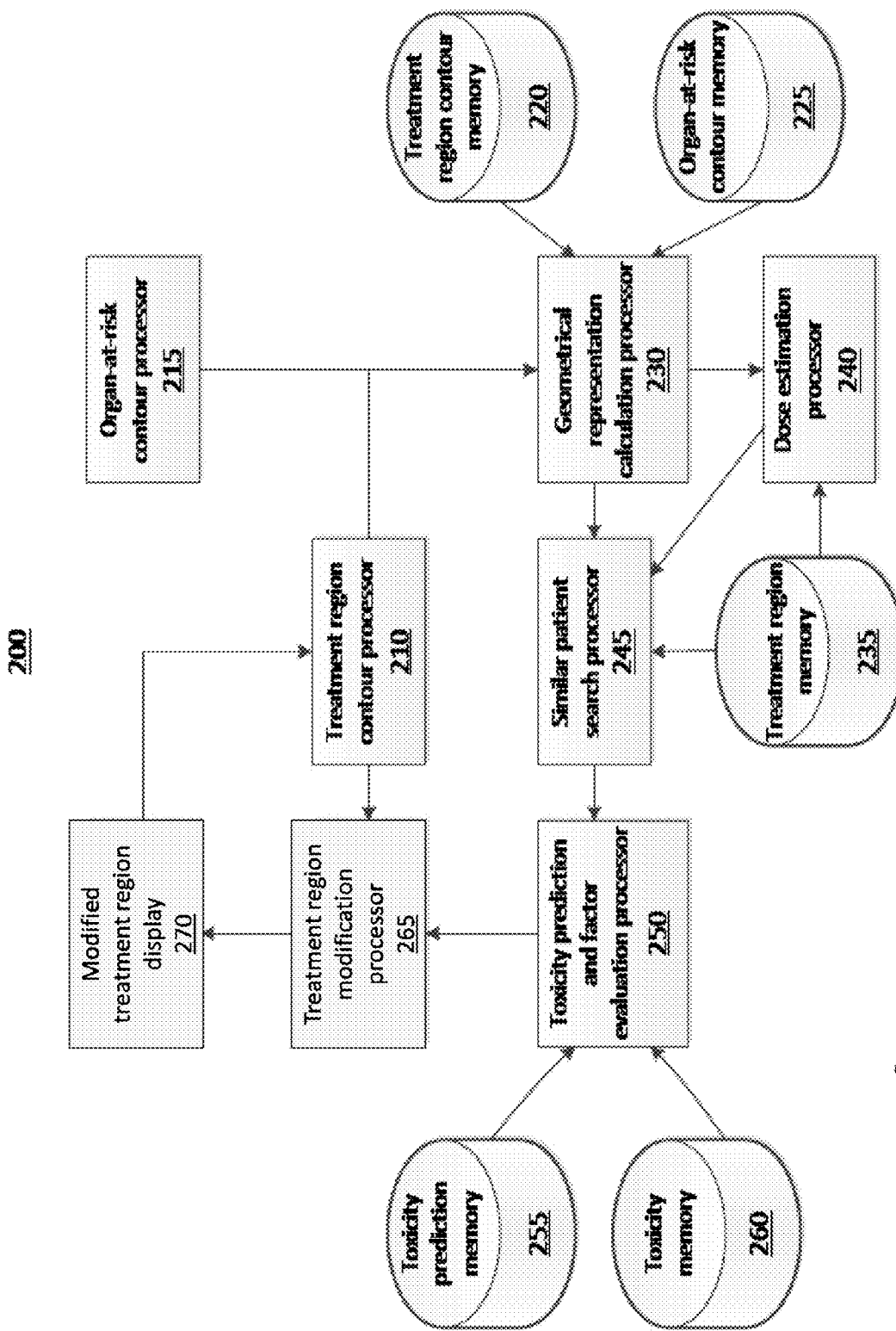
FIG. 2B is a block diagram of an exemplary radiation treatment support system according to an embodiment.
Figure 2C:
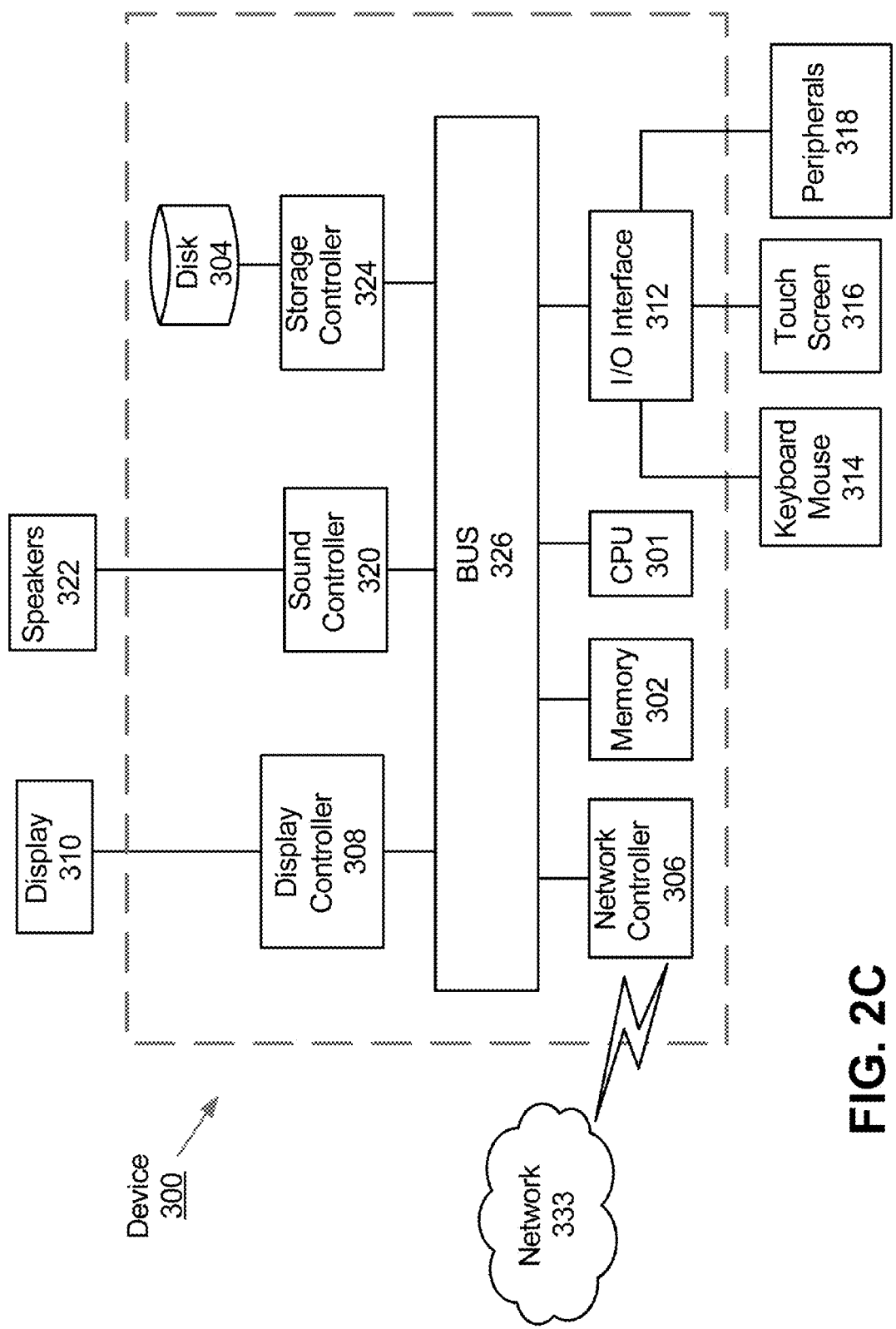
FIG. 2C is a block diagram of a hardware description of a computing device according to an embodiment.
Figure 3:
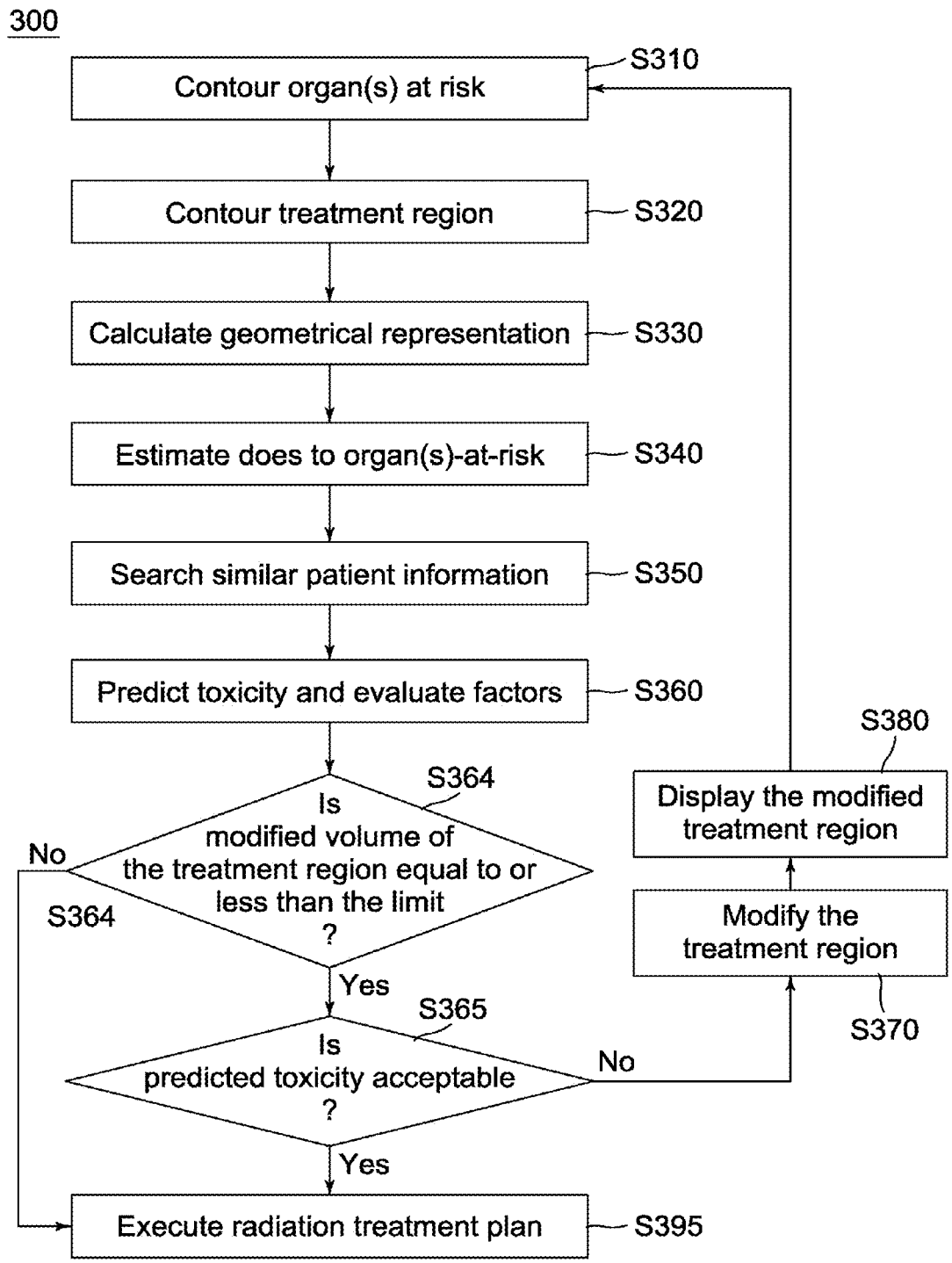
FIG. 3 is an exemplary flowchart for a method of determining a radiation treatment region according to an embodiment.

FIG. 3 is an exemplary flowchart for a method 300 of determining a radiation treatment region. A contour means, e.g., a determined surface of a three-dimensional treatment region of an organ at risk (OAR). A contour of an OAR is determined in step S310 via a contour processor, such as the OAR contour processor 215, which will be described in more detail with reference to FIG. 2B. A contour of a treatment region is determined in step S320 via a contour processor, such as the treatment region contour processor 210 illustrated in FIG. 2. Treatment region contour processor 210 contours a radiation treatment region on one or more medical images, such as a CT image or a MM image or a PET image.

Figure 4:
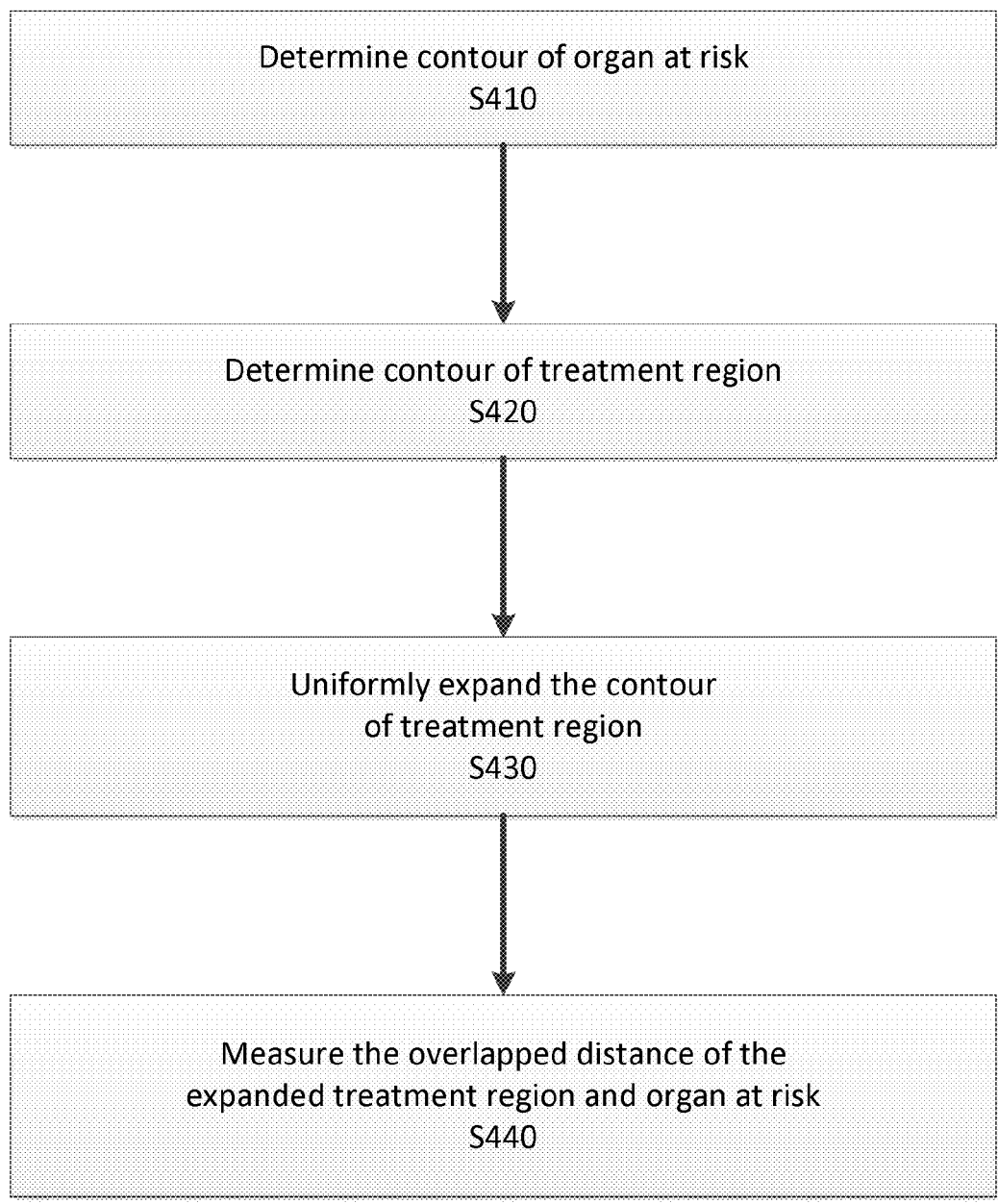
FIG. 4 is an exemplary flowchart for a method of calculating a geometrical representation of the radiation treatment region and one or more OARs according to an embodiment.

A geometrical representation of at least one OAR and the radiation treatment region is calculated in step S330 via the geometrical representation calculation processor 230, which will be described in more detail with reference to FIG. 2B. FIG. 4 is an exemplary flowchart of step S330 for calculating the geometrical representation of the radiation treatment region and of the one or more OARs. A contour of an OAR is determined in step S410, and a contour of the treatment region is determined in step S420. Contours of the OAR and the treatment region can be determined using the OAR contour processor 215 and the treatment region contour processor 210, respectively.

The contour of the treatment region is uniformly expanded in step S430. In one embodiment, the expansion region reaches up to the closest OAR. In another embodiment, the radius of the expansion region extends a fixed distance beyond the treatment region. In still another embodiment, the expansion region extends a certain percentage beyond the radius of the treatment region.

The expanded distance and the overlapped distance are measured in step S440. In another embodiment, the overlapped volume of the expanded treatment region and the OAR are measured in step S440.

Figure 5:
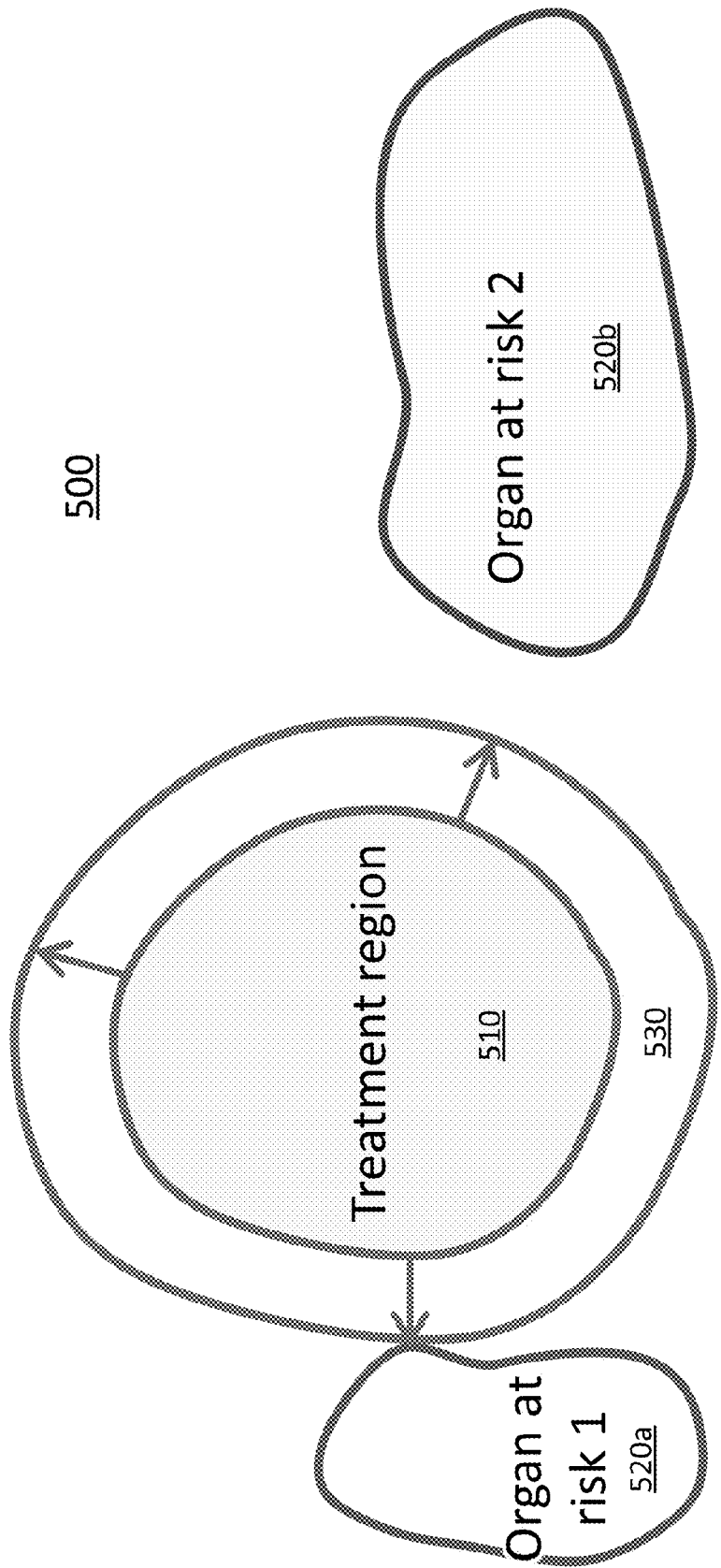
FIG. 5 illustrates a geometrical representation of an expanded treatment region and nearby OARs according to an embodiment.

FIG. 5 illustrates a geometrical representation 500 of an expanded treatment region and nearby OARs. A treatment region 510 includes the area or volume of radiation treatment. A first OAR 520a is in close vicinity to the treatment region 510. A second OAR 520b is in close vicinity to the treatment region 510, but not as close as the first OAR 520a. An expansion region 530 is formed around the treatment region 510. FIG. 5 is illustrated as a two-dimensional arrangement for simplicity. However, an actual geometrical representation would be calculated for a three-dimensional arrangement of the treatment region 510, the OARs 520a and 520b, and the expansion region 530.

Table 1 below illustrates calculated geometries for an exemplary arrangement of OARs and the distance between OARs and the treatment region.

TABLE 1

Calculated geometrical representation

| | Organs at Risk (OAR) | Distance between OARs and treatment region |
|---|---|---|
| 1 | Parotid gland (right) | 1 cm |
| 2 | Parotid gland (left) | 6 cm |
| 3 | Spinal cord | 4 cm |
| 4 | Larynx | 9 cm |
| 5 | Pharynx | 5 cm |
| 6 | Esophagus | 11 cm |

With reference to FIG. 3, the radiation dose to the OAR(s) is estimated in step S340 via a dose estimation processor 240, which will be described in more detail with reference to FIG. 2B. The dose is estimated from prior treatment plans of prior patients with similar geometrical representations. For example, when a distance between a planned target volume and an OAR is below a set threshold, it can be used as a similar geometrical representation. The estimated dose can also be based on a size and type of tumor under radiation treatment.

Figure 6:
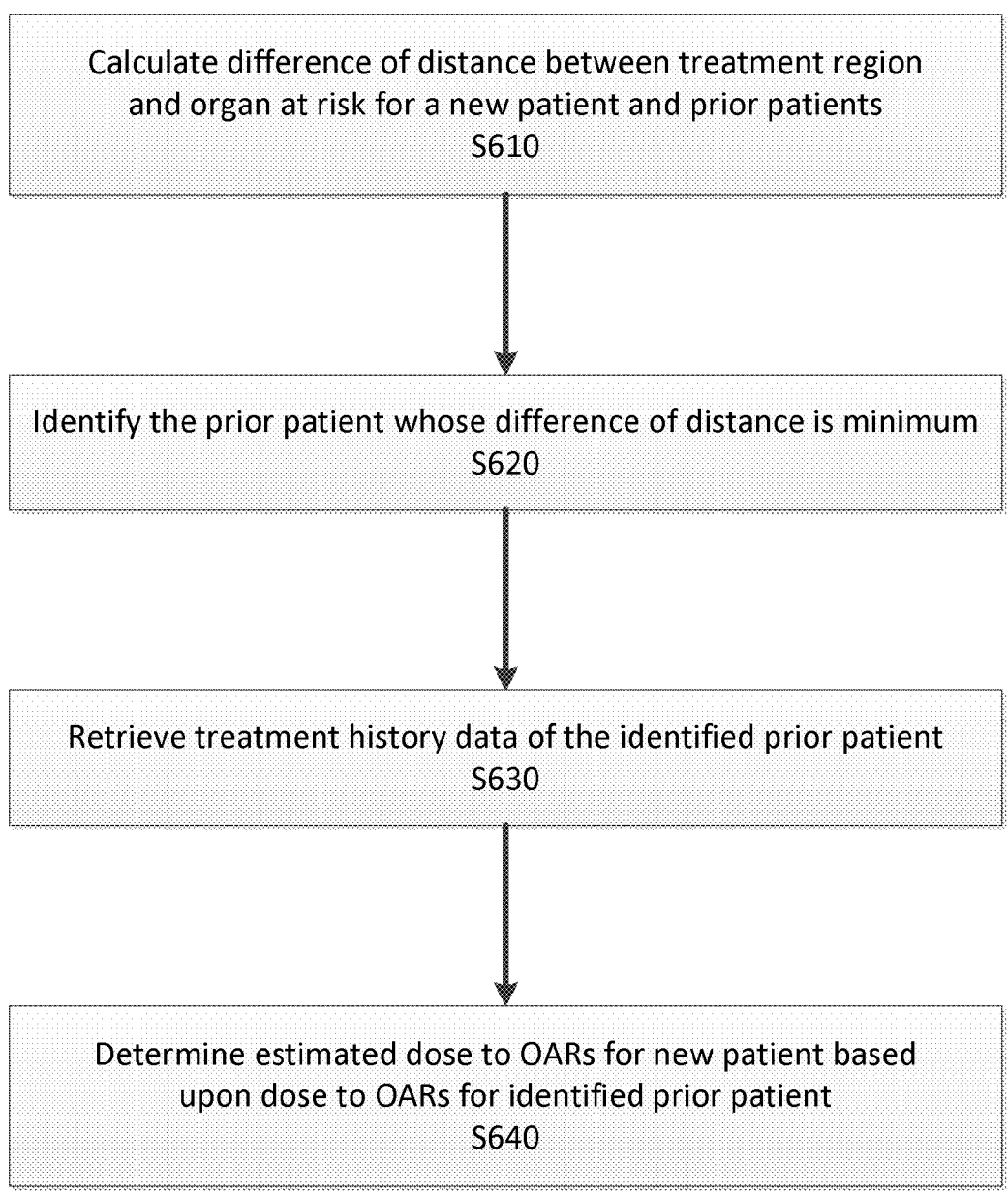
FIG. 6 is an exemplary flowchart for a method of estimating the dosage according to an embodiment.

FIG. 6 is an exemplary flowchart of step S340 for estimating the dose to each OAR. The distance between the treatment region and each OAR is calculated for a new patient in step S610. The distance between the treatment region and each OAR is also calculated for prior patients with similar geometries and factors relative to the new patient, in step S610. Prior patients having a difference of distance within the threshold from the new patient calculated in step S610 are identified in step S620. The treatment history data of the identified prior patients are retrieved in step S630.

The radiation dose to OARs of the identified prior patient is outputted. Based upon the radiation dose for the identified prior patient and other related factors, an estimated dose for the new patient to OARs is determined in step S640.

Table 2 below illustrates the estimated dosage for the new patient from dosage data used from prior patients with similar geometries and other similar factors.

TABLE 2

Estimated dosage for new patient

| | Organs at Risk (OAR) | Estimated dosage to OARs |
|---|---|---|
| 1 | Parotid gland (right) | 30 Gy |
| 2 | Parotid gland (left) | 20 Gy |
| 3 | Spinal cord | 40 Gy |
| 4 | Larynx | 40 Gy |
| 5 | Pharynx | 30 Gy |
| 6 | Esophagus | 20 Gy |

With reference to FIG. 3, similar patient information is searched in step S350 via a similar patient search processor 245, which will be described in more detail with reference to FIG. 2B. The similar patient search processor 245 searches for prior patients with similar geometrical representations and/or similar estimated doses.

Figure 7:
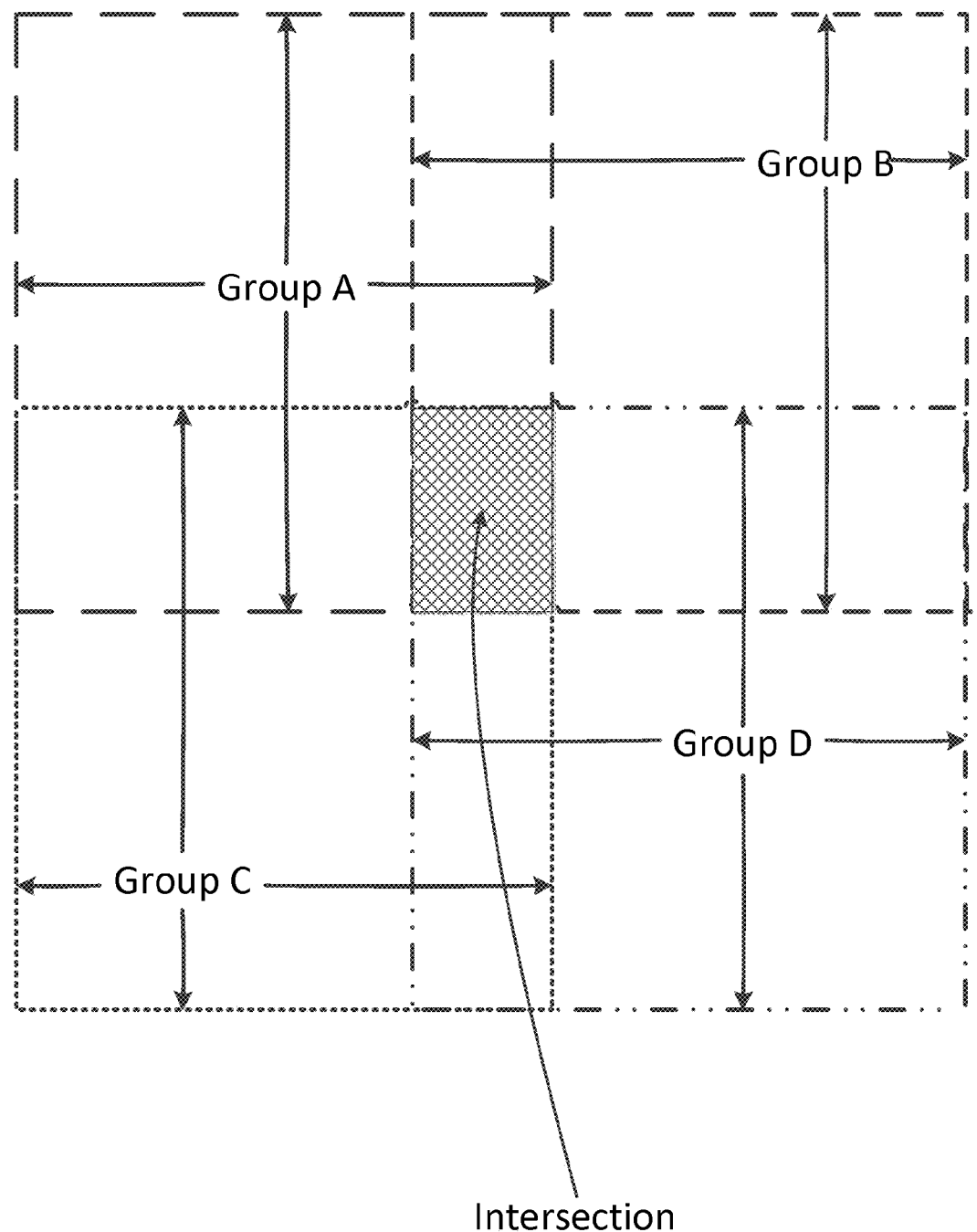
FIG. 7 is an illustration representing an intersection of multiple factors present in prior patients according to an embodiment.

FIG. 7 is an illustration representing an intersection of multiple factors present in prior patients. Patient demographics, diagnoses, and assessment records can be used for searching similar patients. In FIG. 7, Group A could represent prior patients whose difference of dose to an OAR is within a certain threshold. Group A is represented by the long hashed perimeter. Group B could represent prior patients whose difference of distance between a treatment region and an OAR is within a certain threshold. Group B is represented by the short hashed perimeter. Group C could represent prior patients with similar demographics. Group C is represented by the dotted perimeter. Group D could represent prior patients with similar diagnoses. Group D is represented by the alternating hash/dotted perimeter. The identified intersection in FIG. 7 represents those prior patients of interest having factors in all four of Groups A, B, C, and D.

Figure 8:
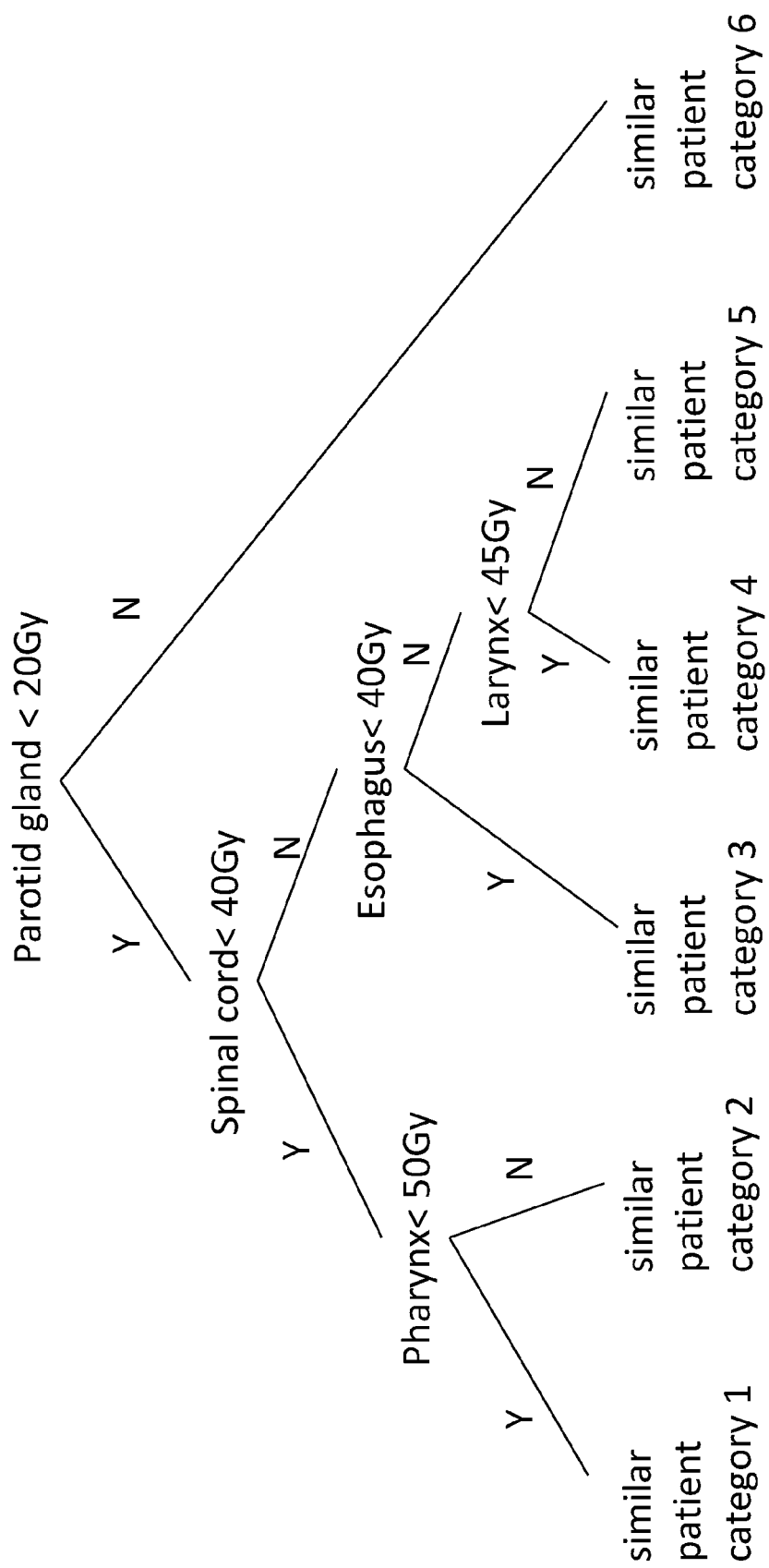
FIG. 8 illustrates grouping similar patients using a decision tree according to an embodiment.

FIG. 8 illustrates an embodiment in which similar patients can be grouped using a decision tree. In one embodiment, patients are grouped into a similar patient category by combinations of splitting threshold criteria of radiation dose to OARs. For example, in FIG. 8, patients are grouped into six groups by radiation dose to the parotid, the spinal cord, the esophagus, the pharynx, and the larynx. FIG. 8 is given for illustrative purposes only for an example in which the treatment region is within the head and neck. However, embodiments described herein can be used for other regions of the body and other associated OARs. In addition, more or less than six similar patient categories can be used in embodiments described herein.

FIG. 8 illustrates that patients in category 1 received less than a 50 Gy dose to the pharynx, while patients in category 2 did not receive less than a 50 Gy dose to the pharynx. Patients in category 1 received less than a 40 Gy dose to the spinal cord, while patients in category 5 did not receive less than a 40 Gy dose to the spinal cord. Patients in category 1 received less than a 20 Gy dose to the parotid gland, while patients in category 6 did not receive less than a 20 Gy dose to the parotid gland. Patients in category 3 received less than a 40 Gy dose to the esophagus, while patients in category 5 did not receive less than a 40 Gy dose to the esophagus. Patients in category 4 received less than a 45 Gy dose to the larynx, while patients in category 5 did not receive less than a 45 Gy dose to the larynx.

With reference to FIG. 3, toxicity and evaluation factors are predicted in step S360 via a toxicity prediction and factor evaluation processor 250, which will be described in more detail with reference to FIG. 2B. The toxicity prediction and factor evaluation processor 250 predicts the presence or probability of radiation toxicity and evaluates relevant OARs based on the predicted toxicity.

Figure 9:
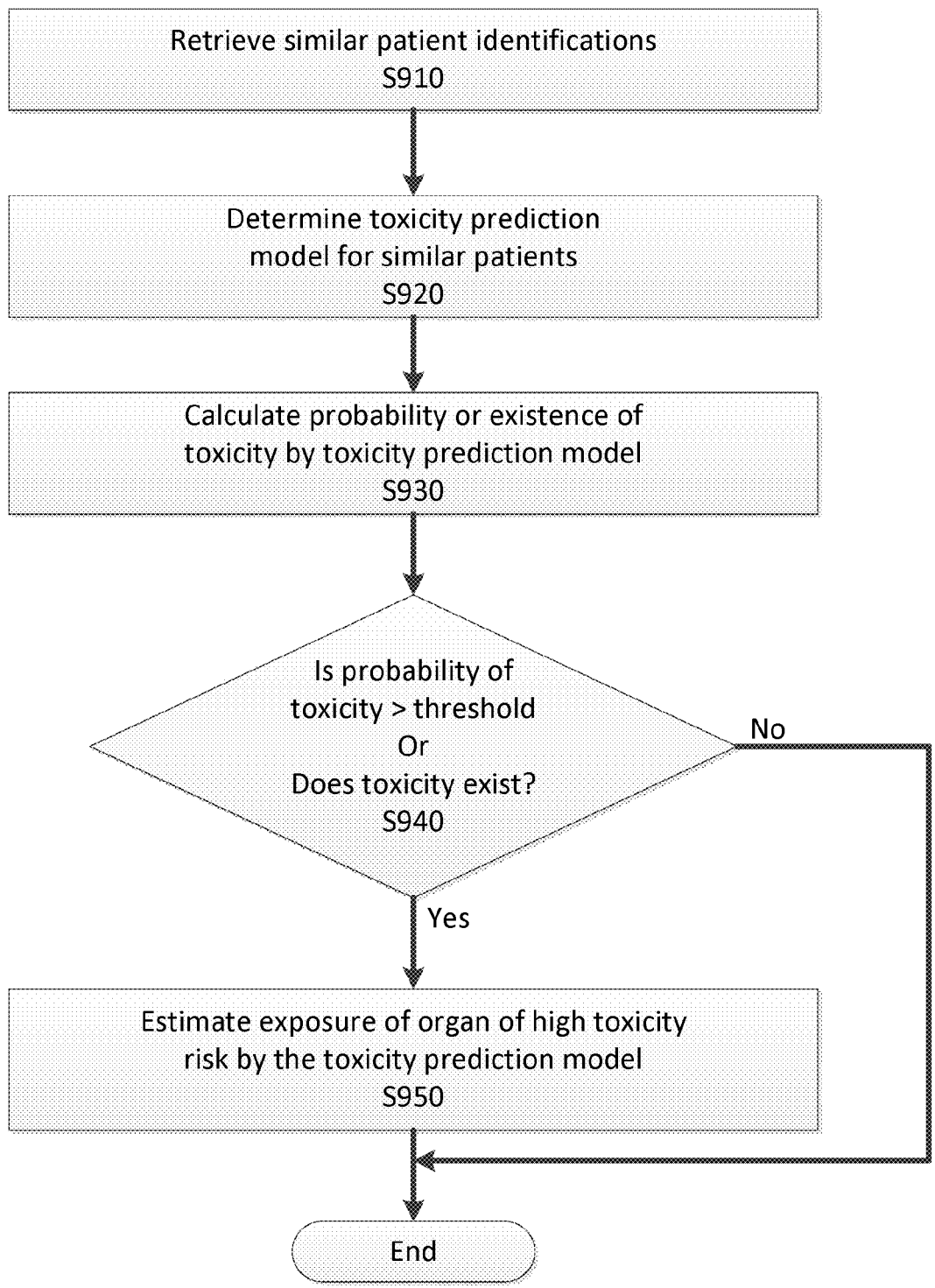
FIG. 9 is an exemplary flowchart for a method of predicting toxicity and evaluating factors according to an embodiment.

FIG. 9 is an exemplary flowchart of step S360 for predicting and evaluating toxicity. Similar patient identifications are retrieved in step S910. A toxicity prediction model for a group of similar patients is determined in step S920. A probability or existence of toxicity is calculated by the toxicity prediction model in step S930.

In step S940, it is determined whether a probability of toxicity is greater than a given threshold or if the toxicity exists. For example, the given threshold for the probability of toxicity is 0.80. If the probability of toxicity is greater than the threshold or is present (a "yes" decision in step S940), the toxicity exposure for an organ of high toxicity risk is estimated by the toxicity prediction model in step S950. If the probability of toxicity is not greater than the threshold or is not present (a "no" decision in step S940), the process ends.

Figure 10:
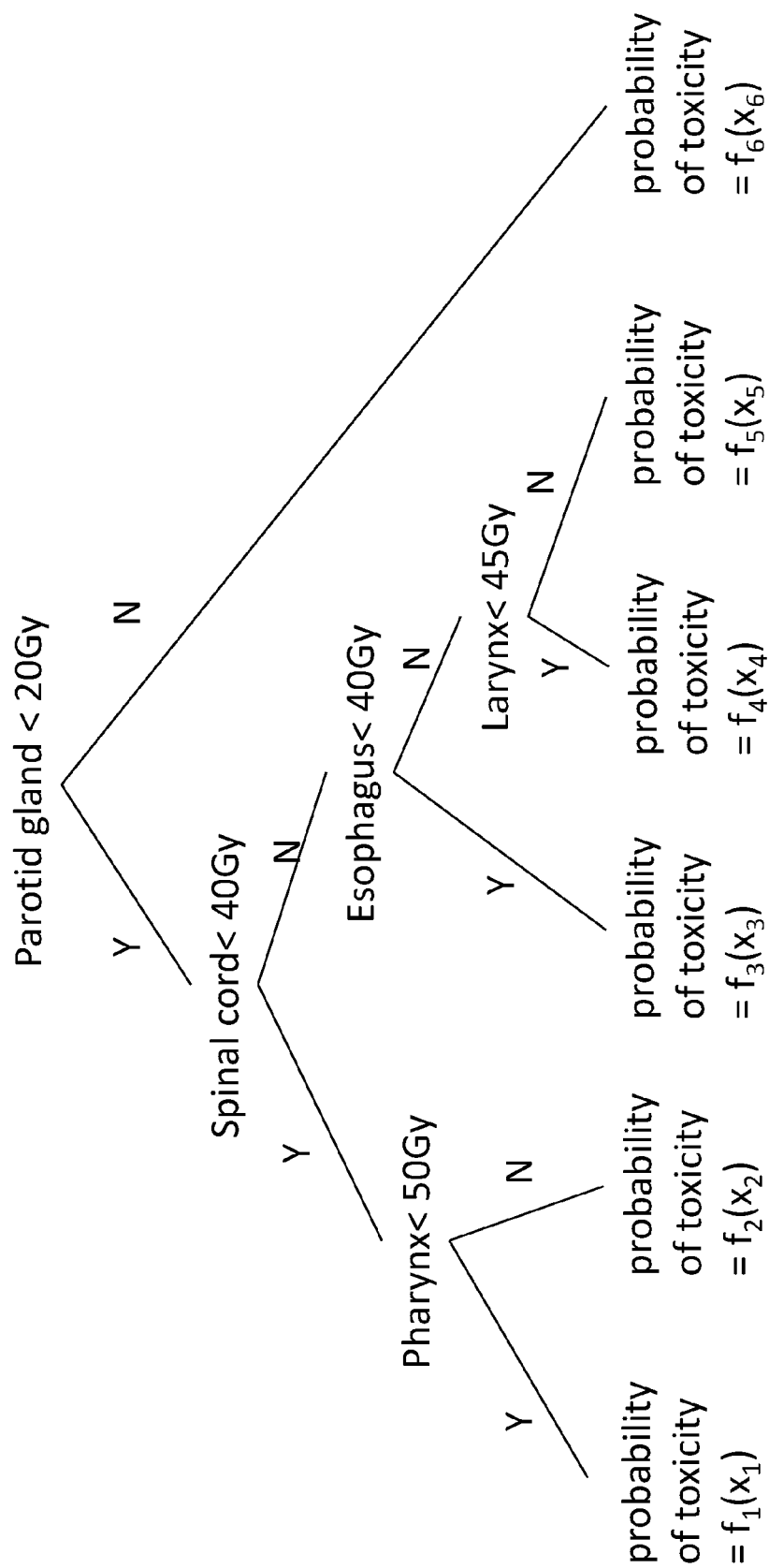
FIG. 10 illustrates a toxicity prediction model according to an embodiment.

FIG. 10 illustrates a toxicity prediction model, which is used for each of the similar patient categories of FIG. 8. For example, a toxicity prediction model $f_1(x_1)$ is used for similar patient category 1 to determine the probability of toxicity when the parotid gland has received less than a 20 Gy radiation dose, the spinal cord has received less than a 40 Gy radiation dose, and the pharynx has received less than a 50 Gy radiation dose. Similarly, a toxicity prediction model $f_4(x_4)$ is used for similar patient category 1 to determine the probability of toxicity when the parotid gland has received less than a 20 Gy radiation dose, the spinal cord has not received less than a 40 Gy radiation dose, the esophagus has not received less than a 40 Gy radiation dose, and the larynx has received less than a 45 Gy radiation dose. In a similar way, toxicity prediction models are determined for the other similar patient categories.

Various prediction models can be used with embodiments described herein, such as the Nadaraya-Watson density estimation model, a decision-tree model, or a logistic regression model, as described herein with reference to the toxicity prediction and factor evaluation processor 250. A toxicity prediction result for a patient is illustrated in Table 3 below.

TABLE 3

| Toxicity prediction result |
| --- |
| ICD-9 = 146.6 (Oropharynx) |
| Tumor staging: T2N1M0 |
| Male, 65 years old |
| Estimated dose: (see Table 2) |
| Probability of toxicity: 0.8 (high) |

Table 4 below illustrates an evaluation of high toxicity for an OAR, as determined by a toxicity prediction model.

TABLE 4

| Evaluated OARs for high toxicity | | | |
| --- | --- | --- | --- |
| Organs at Risk (OAR) | Estimated dose to organs at risk | Parameter of toxicity prediction model | Organs having high toxicity risk |
| 1 Parotid gland (right) | 30 Gy | 20 Gy | Y |
| 2 Parotid gland (left) | 15 Gy | 20 Gy | N |
| 3 Spinal cord | 30 Gy | 40 Gy | N |
| 4 Larynx | 30 Gy | 45 Gy | N |
| 5 Pharynx | 35 Gy | 50 Gy | N |
| 6 Esophagus | 20 Gy | 40 Gy | N |

Table 4 illustrates the evaluation of high toxicity for various organs from the toxicity prediction model, illustrated in FIG. 10. In Table 4, the right parotid is evaluated as an organ of high toxicity risk, since the dose is above the established parameter.

Figure 11:
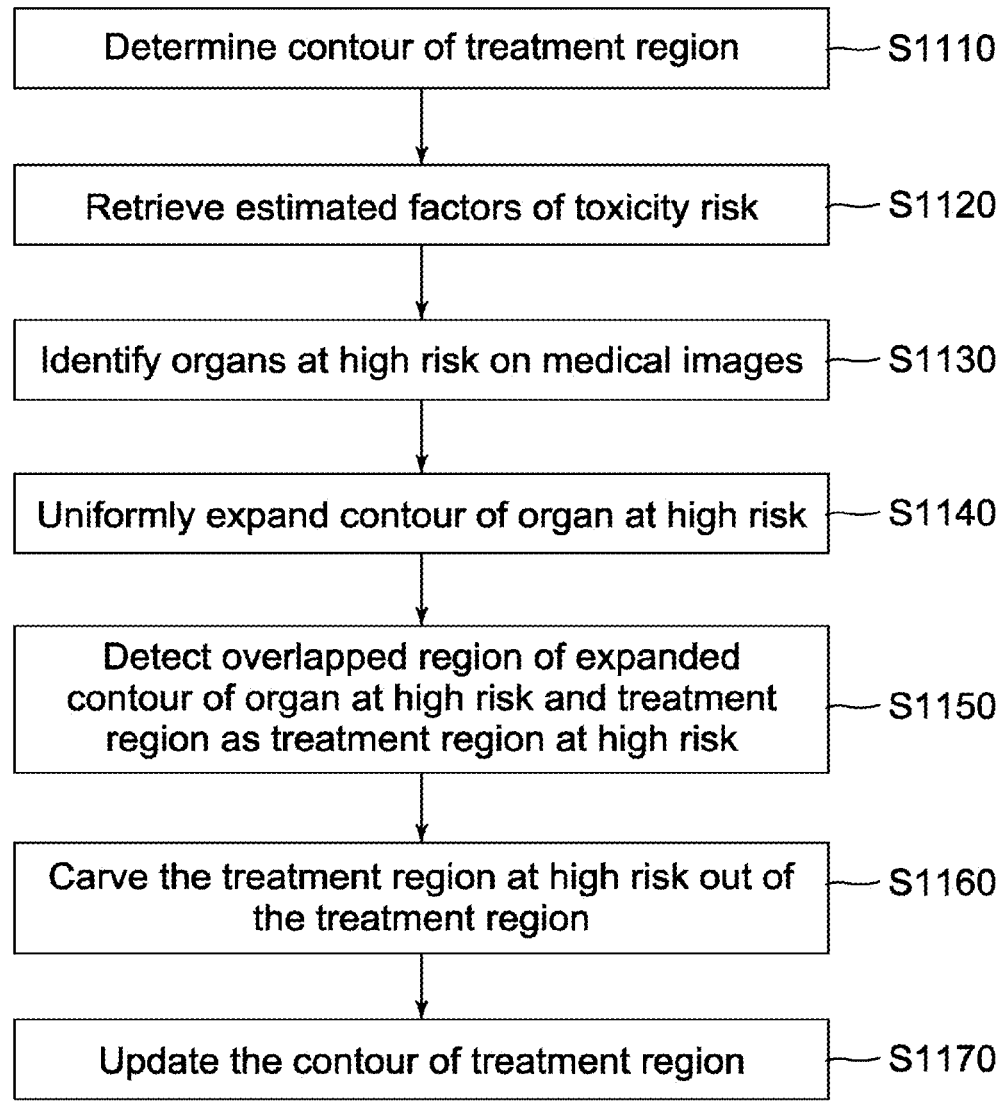
FIG. 11 is an exemplary flowchart for a method of modification of a treatment region according to an embodiment.

With reference to FIG. 3, a treatment region is modified in step S370 via a treatment region modification processor 265, which will be described in more detail with reference to FIG. 2B, to determine an area within the treatment region close to any relevant OARs of the predicted toxicity. FIG. 11 is an exemplary flowchart of step S370 for a modification of the treatment region. A contour of the treatment region is determined in step S1110. The evaluated OARs having toxicity risk are retrieved in step S1120. Any organs at high risk are identified on subject medical images in step S1130.

The contour of each organ at high risk is uniformly expanded in step S1140. Step S1140 can be configured to expand the contour of the identified organ until the volume of the overlapped region reaches a specified volume. In another embodiment, the contour of the identified organ region extends a fixed distance beyond the treatment region. In still another embodiment, the expansion region extends a certain percentage beyond the radius of the treatment region. In one embodiment, the specified volume is equal to or less than a limit in S364 specified by a percentage of the volume of the original treatment region determined by the initial contour of the treatment region. For example, a limit in S364 can be 10 percent of the volume of the original treatment region. For example, when the volume of the original treatment region is 500 cc, the limit is 50 cc. In this case, the specified volume in Step S1140 can be either of 10 cc, 20 cc, 30 cc, 40 cc, and 50 cc, for example. In this example, 10 cc is an incremental unit of the specified volume, but the incremental unit can be arbitrary. The specified volume in Step S1140 can be incrementally increased from 10 cc to 50 cc, while repeating, for the modified treatment region, the steps of determining the contour of the treatment region in Step S320, predicting the radiation toxicity in Step S360, and determining the predicted radiation toxicity in Step S365 until it is determined that the predicted radiation toxicity does not exceed the given threshold. For example, the given threshold for the predicted probability of toxicity in Step 365 can be 0.80.

The respective region in which the expanded contour of each organ at high risk overlaps the treatment region is detected and identified as a treatment region at high risk in step S1150. The treatment region at high risk can be carved out of the treatment region in S1160 and the treatment region can be updated in S1170.

Figure 12A:
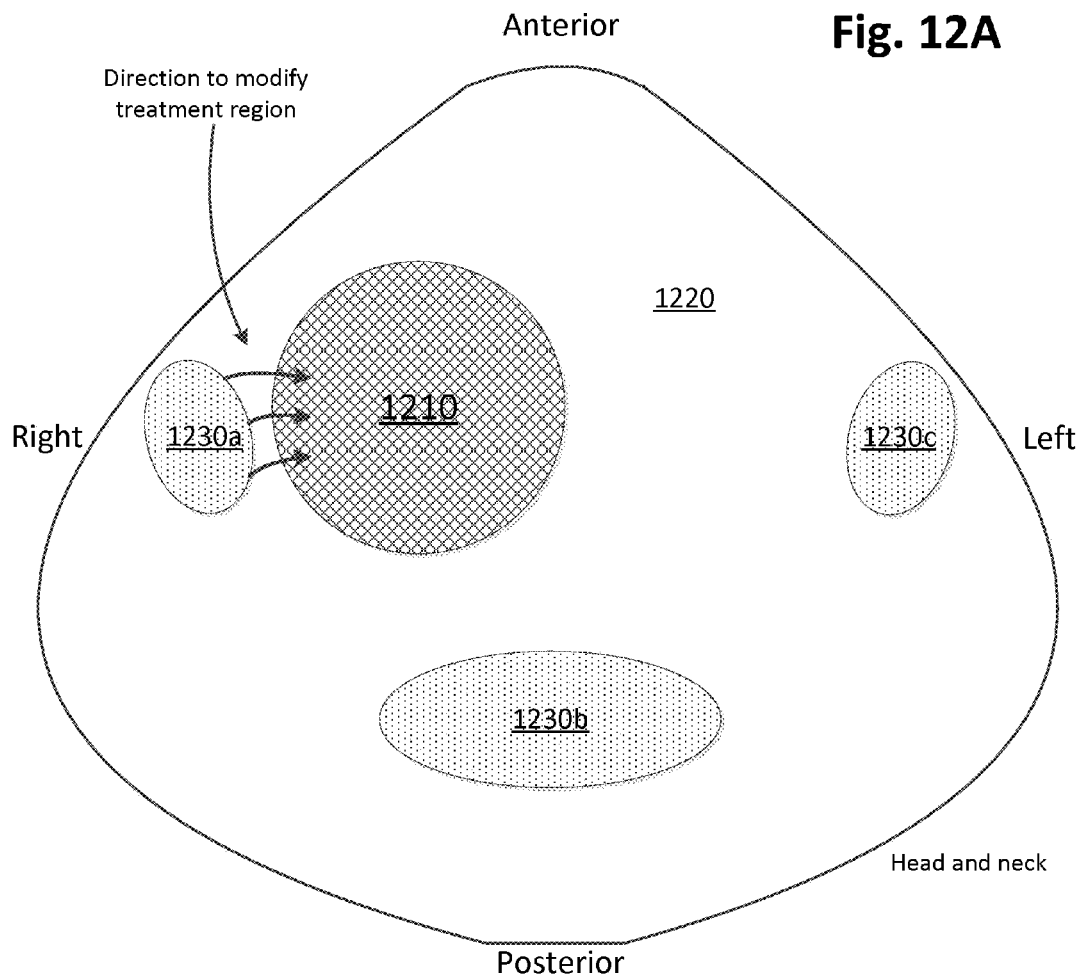
FIG. 12A illustrates a modified treatment region display of a treatment region according to an embodiment.

With reference to FIG. 3, the modified treatment region is displayed in step S380 via a modified treatment region display 270, which will be described in more detail with reference to FIG. 2B. The modified treatment region display 270 displays the contour of the treatment region, the determined area of the treatment region, and the predicted toxicity. FIG. 12A illustrates a region evaluation result display of a treatment region 1210 within the head and neck region 1220 of a patient. The treatment region 1210 is close to an OAR 1230*a*. Two other OARs 1230*b* and 1230*c* are in the vicinity of the treatment region 1210. FIG. 12A illustrates a direction to modify the contour of the treatment region where an extended region of the OAR 1230*a* partially overlaps the treatment region 1210. The table illustrated in FIG. 12A shows the OAR is the right parotid gland. The estimated dose to the right parotid gland is 30 Gy. It is notated that this is an organ of high toxicity risk at this dose.

FIG. 12B illustrates the region evaluation result display after modification of the treatment region. The treatment region 1210 has been carved away from the OAR 1230*a* where the extended OAR 1230*a* partially overlapped the treatment region 1210. The table illustrated in FIG. 12B shows that the right parotid gland will have an estimated dose of 20 Gy after modification of the treatment region 1210, which removes it from the high toxicity risk category at the new dose level.

With reference to FIG. 3, a determination is made in step S364 if the difference of the volume between the volume of the original treatment region determined by the initial contour of the treatment region and the volume of the modified treatment region is acceptable.

For example, an acceptable difference of the volume occurs when the difference of the volume is equal to or less than the limit specified by a percentage of the volume of the original treatment region determined by the initial contour of the treatment region. When the evaluation result is acceptable (a "yes" decision in step S364), a determination is made in step S365 whether the predicted toxicity is acceptable.

When the evaluation result is not acceptable (a "no" decision in step S364, which is a stopping condition), the radiation treatment plan is executed in step S395.

In another embodiment, a determination is made in step S364 whether the number of iterations of modifying the contour of the treatment region is equal to or less than the preselected number of iterations. For example, when the number of iterations of modifying the contour of the treatment region is equal to or less than the preselected number of iterations such as 10 (a "yes" decision in step S364), a determination is made in step S365 whether the predicted toxicity is acceptable. When the number of iterations of modifying the contour of the treatment region is greater than the preselected number of iterations (a "no" decision in step S364, which is a stopping condition), the radiation treatment plan is executed in step S395.

With reference to FIG. 3, a determination is made in step S365 whether the predicted toxicity is acceptable. For example, an acceptable predicted toxicity occurs when the evaluated probability of toxicity is less than a given threshold or when the evaluated toxicity does not exist. If the predicted toxicity is not acceptable (a "no" decision in step S365), the treatment region is modified in step S390, such as the modification illustrated in FIGS. 12A and 12B. After modifying the contour of the treatment region in step S390, the process returns to step S320 to contour the treatment region and to repeat the process again until the evaluation result in step S365 is acceptable. For example, the given threshold for the predicted probability of toxicity in Step 365 can be 0.80. When the evaluation result t is acceptable (a "yes" decision in step S365, which is a stopping condition), the radiation treatment plan is executed in step S395.

FIG. 12B illustrates just one modification made to bring the OAR out of the high toxicity risk category for simplicity. However, several modifications can be made in real-time to gradually bring an OAR out of the high toxicity risk category, as illustrated in FIG. 3. For example, if the modified treatment region illustrated in FIG. 12B did not remove the OAR from the high toxicity risk category, the process returns to step S320 of FIG. 3 to contour the modified treatment region. Method 300 proceeds to calculate a geometrical representation of the modified region in step S330, estimate the radiation dose to the OAR from the modified treatment region in step S340, search similar patient information regarding the modified treatment region in step S350, predict the modified toxicity and evaluation factors in step S360, evaluate the treatment region in step S370, and display the modified treatment region in step S380.

FIG. 2A is a block diagram illustrating an exemplary structure used in conjunction with embodiments described herein. A radiation therapy device 25, such as a LINAC causes a radiation source to provide radiation to a treatment region of a patient. The radiation therapy device 25 is controlled by at least one central processing unit (CPU) 35. The CPU 35 controls the radiation therapy device 25 to deliver a programmed radiation treatment regimen to the patient. A memory device 45 stores data that can be retrieved by the CPU 35. The data includes information (e.g., databases) of prior and present patients and their associated radiation treatment regimens.

A display device 55 displays the treatment region and surrounding OARs. The display device 55 refreshes the treatment region to illustrate any modifications made to the treatment region. For example, if an OAR is exposed to a radiation dosage above recommendations, the treatment region can be modified to lower the radiation dosage to the OAR. The modified treatment region is displayed on the display device 55.

FIG. 2B is a block diagram of an exemplary radiation treatment support system 200 used in conjunction with embodiments described herein. Radiation treatment support system 200 includes multiple processors, wherein each of the processors is implemented via one or more central processing units (CPUs) controlled by associated software and/or as specialized circuitry.

The treatment region contour processor 210 is configured to determine a contour of a treatment region on medical images, such as medical images obtained from a CT scanner or from magnetic resonance imaging (MM) or from positron emission tomography imaging (PET). Treatment regions include but are not limited to, a planning target volume (PTV), a gross tumor volume (GTV), a clinical target volume (CTV), and an internal target volume (ITV). Planning target volumes include volumes for multiple doses, such as high dose PTV (70 Gy), medium dose PTV (50 Gy), and low dose PTV (40 Gy). Conventional image segmentation algorithms can be used to obtain the contours, such as amplitude segmentation, edge-based segmentation, region-based segmentation, a deformable-model-based method, and an atlas-based segmentation. Amplitude segmentation is executed in the following equation.

$$r_{i,j} = \begin{cases} 1, & p_{i,j} \geq T \\ 0, & p_{i,j} < T \end{cases}$$

Where $r_{i,j}$ is the resulting pixel of 0-1 segmentation at coordinate (i, j), $p_{i,j}$ is the pixel of input image, and T is the value of threshold for segmentation.

Alternatively, the contours can be specified manually by an operator.

The OAR contour processor 215 is used to determine a contour of one or more OARs on one or more medical images, such as CT or MRI or PET images. The OAR contour processor 215 transmits processed instructions and data to the geometrical representation calculation processor 230.

The treatment region contour memory 220 stores data from contours of treatment regions of new patients and prior patients. Similarly, the OAR contour memory 225 stores data from contours of OARs of new patients and prior patients. Treatment region contour memory 220 and OAR contour memory 225 transmits data for processing to the geometrical representation calculation processor 230.

The geometrical representation calculation processor 230 is configured to calculate geometrical representations between a radiation treatment region and an OAR for both new patients and prior patients. The calculated geometrical representations are transmitted to the similar patient search processor 245.

An overlap volume histogram (OVH) is a method of calculating the geometric representation, where OVH can be represented as:

$$OVH(r) = \frac{|\{p \in O \mid d(p,T) \leq r\}|}{|O|}$$

where
d(p,T): distance between point p and T
||: volume of an object, O: OAR, T: PTV surface A minimum distance R between a PTV and an OAR can be used to calculate a geometrical representation, and is represented as:

$$R = \min_{r \in \{OVH(r) > 0\}} r$$

The treatment region memory 235 stores data for a dose volume histogram (DVH) of OARs for new patients and prior patients. The data is transmitted to the dose estimation processor 240 for processing.

The dose estimation processor 240 is configured to estimate a dose to OARs of a patient based upon treatment plans of prior patients with similar geometrical representations. Processed instructions and data are transmitted to the similar patient search processor 245. In an example given for illustrative purposes only, if a first patient has a larger distance from an OAR to the target tumor than a second patient, a lower radiation dose will be received by the OAR of the first patient, as opposed to the OAR of the second patient. Therefore, if a new patient is similar to the first patient, then all prior patients having OARs closer to the target area which require larger doses are found. The prior patient that utilized the lower dose successfully can be used to determine an estimated dose for the new patient. This dose estimation process is applied to one OAR at a time and is repeatedly applied to multiple OARs of interest.

In a second example given for illustrative purposes only, a search is conducted for prior patients that have OVH or R values similar to the new patient. For example, all prior patients can be found whose OVH distances (or R) of the OARs is close to the OVH distances (or R) of OARs in the new patient. The prior patient that utilized the lower dose successfully is used to determine a radiation therapy treatment of the new patient.

The similar patient search processor 245 is configured to search for prior patients having similar geometrical representations and/or similar estimated doses. Data and instructions from the geometrical representation calculation processor 230, the treatment plan memory 235, and the dose estimation processor 240 are used by the similar patient search processor 245. Patient demographics, diagnoses, and/or assessment records are used to search for similar prior patients. In one embodiment, patients with similar geometrical representations are found using the following calculations.

1. Calculate a minimum distance $R_i$ between PTV and the i-th OARs (i=1 ... M) for a new patient and define:

$$\vec{x} = (R_1, R_2, \ldots, R_M) \text{ where}$$

M is the number of selected OARs. M=1 when a single organ at risk is of interest.

2. Calculate the Euclidean distance D between $\vec{x}$ and $\vec{x_j}$ (vector of j-th prior patient)

$$D(\vec{x}, \vec{x_j}) = \sqrt{\sum_{i=1}^{M}(R_i - R_{ij})^2}$$

3. A similar patient group $J_s$ is defined as:

$$J_s = \{j \in J \mid K(D(\vec{x}, \vec{x_j})) < d\} \text{ where}$$

$$K(u) = \frac{1}{\sqrt{2\pi}} e^{-\frac{u^2}{2\sigma^2}}$$

K(u): Gaussian kernel function
σ: kernel parameter

In a second embodiment, similar patients can be grouped by a decision tree. For example, patients can be grouped into similar patient categories by combinations of splitting threshold criteria of dosage to an OAR, which is illustrated in FIG. 8.

The toxicity prediction and factor evaluation processor 250 is configured to predict the presence or probability of radiation toxicity and evaluate relevant OARs using the predicted toxicity. Processed instructions and data are received from the similar patient search processor 245.

The toxicity memory 260 stores toxicity data and is used in conjunction with the toxicity prediction and factor evaluation processor 250. The toxicity prediction memory 255 is used in conjunction with the toxicity prediction and factor evaluation processor 250. Predicting the presence or probability of radiation toxicity can be realized by a prediction model for each of similar patient groups whose data is stored in the toxicity prediction memory 255. For example, a prediction model can be a Nadaraya-Watson density estimation model that calculates $\hat{f}(\vec{x})$, a weighted average of similar patients' toxicity based on the geometrical representation. Toxicity estimation for $\vec{x}$ by the Nadaraya-Watson density estimation is given by:

$$\hat{f}(\vec{x}) = \frac{\sum_{j \in J_S} K(D(\vec{x}, \vec{x_j})) y_j}{\sum_{j \in J_S} K(D(\vec{x}, \vec{x_j}))}$$

where $$K(u) = \frac{1}{\sqrt{2\pi}} e^{-\frac{u^2}{2\sigma^2}}$$

$y_j$: Toxicity grade of j-th patient
K(u): Gaussian kernel function
σ: kernel parameter A second toxicity prediction model is a decision-tree model. For example, given a patient with a particular estimated dosage, a toxicity prediction model $f_6(x_6)$ is set. $f_6(x_6)$ can be a calculating function of a ratio of patients with high toxicity, given by:

$$f_6(x_6) = \frac{\text{\# patients wigh high toxicity in group 6}}{\text{\#patients in group 6}}$$

Or $f_6(x_6)$ can be another function, like a logistic regression wherein $x_6$ is a vector of explanatory variables, such as the dose to an OAR, the distance between a treatment region and an OAR, demographics, and diagnoses, and $\beta_6$ is a vector of coefficients.

$$f_6(x_6) = \frac{\exp(\beta_6 x_6)}{1 + \exp(\beta_6 x_6)}$$

The treatment region modification processor 265 is configured to determine an area within a treatment region close to the relevant OARs with a predicted factor of high toxicity. Processed instructions and data are transmitted from the treatment region contour processor 210 to the treatment region modification processor 265. The contour of the OAR is uniformly expanded. The contour of the OAR can be configured to expand until the volume of the overlapped region on the treatment region reaches the specified volume.

The overlapped region of the expanded contour of the OAR and the treatment region are detected as the treatment region at high risk. The modified treatment region display 270 is configured to display a contour of the treatment region, the determined area of the treatment region, and the predicted toxicity using processed instructions and data from the treatment region modification processor 265. If the contour of the treatment region is modified, a radiation dose to the OARs is re-estimated from the new contour. The toxicity resulting from the new contour of the treatment region is evaluated by the toxicity prediction model. The modified treatment region data is transmitted to the treatment region contour processor 210.

A hardware description of a computing device 300 according to exemplary embodiments is described with reference to FIG. 2C, such as system controller 110, reconstruction device 114, storage device 112, display device 116 and/or input device 115 illustrated in FIG. 1. Computing device 300 includes a CPU 301 which performs the processes described above and herein after. The process data and instructions can be stored in memory 302. These processes and instructions can also be stored on a storage medium disk 304 such as a hard drive (HDD) or portable storage medium or can be stored remotely. Further, the claimed features are not limited by the form of the computer-readable media on which the instructions of the process are stored. For example, the instructions can be stored on CDs, DVDs, in FLASH memory, RAM, ROM, PROM, EPROM, EEPROM, hard disk or any other information processing device with which the computing device 300 communicates, such as a server or computer.

The claimed features can be provided as a utility application, background daemon, or component of an operating system, or combination thereof, executing in conjunction with CPU 301 and an operating system such as Microsoft Windows 7, UNIX, Solaris, LINUX, Apple MAC-OS and other systems known to those skilled in the art.

The computing device 300 can be realized by various processing circuitry elements. For example, CPU 301 can be a Xenon or Core processor from Intel of America or an Opteron processor from AMD of America, or can be other processor types that would be recognized by one of ordinary skill in the art. Alternatively, the CPU 301 can be implemented on an FPGA, ASIC, PLD or using discrete logic circuits, as one of ordinary skill in the art would recognize. Further, CPU 301 can be implemented as multiple processors cooperatively working in parallel to perform the instructions of the inventive processes described above and below.

The computing device 300 in FIG. 2C also includes a network controller 306, such as an Intel Ethernet PRO network interface card from Intel Corporation of America, for interfacing with network 333. As can be appreciated, the network 333 can be a public network, such as the Internet, or a private network such as an LAN or WAN network, or any combination thereof and can also include PSTN or ISDN sub-networks. The network 333 can also be wired, such as an Ethernet network, or can be wireless such as a cellular network including EDGE, 3G and 4G wireless cellular systems. The wireless network can also be WiFi, Bluetooth, or any other wireless form of communication that is known.

The computing device 300 further includes a display controller 308, such as a NVIDIA GeForce GTX or Quadro graphics adaptor from NVIDIA Corporation of America for interfacing with display 310, such as a Hewlett Packard HPL2445w LCD monitor. A general purpose I/O interface 312 interfaces with a keyboard and/or mouse 314 as well as a touch screen panel 316 on or separate from display 310. General purpose I/O interface 312 also connects to a variety of peripherals 318 including printers and scanners, such as an OFFICEJET or DESKJET from Hewlett Packard.

A sound controller 320 is also provided in the computing device 300, such as SOUNDBLASTER X-FI TITANIUM from Creative, to interface with speakers/microphone 322 thereby providing and/or receiving sounds and/or music.

The general purpose storage controller 324 connects the storage medium disk 304 with communication bus 326, which can be an ISA, EISA, VESA, PCI, or similar, for interconnecting all of the components of the computing device 300. A description of the general features and functionality of the display 310, keyboard and/or mouse 314, as well as the display controller 308, storage controller 324, network controller 306, sound controller 320, and general purpose I/O interface 312 is omitted herein for brevity.

Embodiments herein describe a radiation treatment apparatus including a radiation source configured to provide radiation to a treatment region in a patient according to a radiation treatment regimen. The radiation treatment apparatus also includes a computer processor configured to determine a contour of at least one OAR adjacent to the treatment region, and to determine a contour of the treatment region. The computer processor is also configured to predict a radiation toxicity to the at least one OAR based on the determined contours and the radiation treatment regimen, and to determine whether the predicted radiation toxicity exceeds a threshold. The processor is also configured to modify the contour of the treatment region and repeat, for the modified treatment region, the steps of determining the contour of the treatment region, predicting the radiation toxicity, and determining the predicted radiation toxicity when it is determined that the predicted radiation toxicity exceeds the threshold. The processor is also configured to cause the radiation source to provide the radiation to the treatment region according to the radiation treatment regimen when it is determined that the predicted radiation toxicity does not exceed the threshold.

The computer processor of the radiation treatment apparatus can also be configured to retrieve estimated factors of radiation toxicity risk to the at least one OAR, uniformly expand a contour of an identified organ of high toxicity risk, and detect an overlapped region of the uniformly expanded contour of the identified organ of high toxicity risk and the treatment region. The overlapped region can be detected using an overlap volume histogram method.

The computer processor of the radiation treatment apparatus can be configured to predict the radiation toxicity to the at least one OAR, to retrieve data for at least one prior patient having treatment factors similar to the patient, determine a toxicity prediction model for the at least one prior patient using the treatment factors, calculate a probability of toxicity for the patient using the determined toxicity prediction model, and identify an organ of high toxicity risk using the determined toxicity prediction model. The computer processor can also be configured to retrieve the data for the at least one prior patient using the treatment factors, which include at least one of a geometrical representation of the treatment region and the at least one OAR, an estimated radiation dose to the at least one OAR, patient demographics, patient diagnoses, and patient assessment records. The computer processor can also be configured to determine the toxicity prediction model as one of a Nadaraya-Watson density estimation model and a decision tree model and a logistic regression model.

Embodiments herein describe another radiation treatment apparatus including a radiation source configured to provide radiation to a treatment region in a patient according to a radiation treatment regimen. The radiation treatment apparatus also includes a computer processor configured to determine a contour of at least one OAR adjacent to the treatment region, and to determine a contour of the treatment region. The computer processor is also configured to calculate a geometrical representation of the treatment region and the at least one OAR. The computer processor is also configured to estimate a radiation dose to the at least one OAR using the calculated geometrical representation and the radiation treatment regimen, and to predict a radiation toxicity to the at least one OAR using the estimated radiation dose to the at least one OAR.

The computer processor of the radiation treatment apparatus can also be configured to calculate the geometrical representation of the treatment region to uniformly expand the contour of the treatment region, and measure an overlapped region of the uniformly expanded contour of the treatment region and the at least one OAR. The computer processor can also be configured to uniformly expand the contour of the treatment region using an overlap volume histogram method.

The computer processor of the radiation treatment apparatus can also be configured to estimate the radiation dose to the at least one OAR to calculate a difference in distance between the treatment region and the at least one OAR for the patient and for at least one prior patient, and identify a prior patient with a minimum difference in distance. In addition, the computer processor can be configured to retrieve treatment history data of the identified prior patient, and determine an estimated radiation dose to the at least one OAR for the patient based upon a radiation dose to the identified prior patient.

The computer processor of the radiation treatment apparatus can also be configured to predict the radiation toxicity to the at least one OAR to retrieve data for at least one prior patient having treatment factors similar to the patient, determine a toxicity prediction model for the at least one prior patient, calculate a probability of radiation toxicity for the patient using the determined toxicity prediction model, and identify an organ of high toxicity risk using the determined toxicity prediction model. The computer processor can also be configured to determine the toxicity prediction model as one of a Nadaraya-Watson density estimation model and a decision tree model and a logistic regression model.

Figure 13:
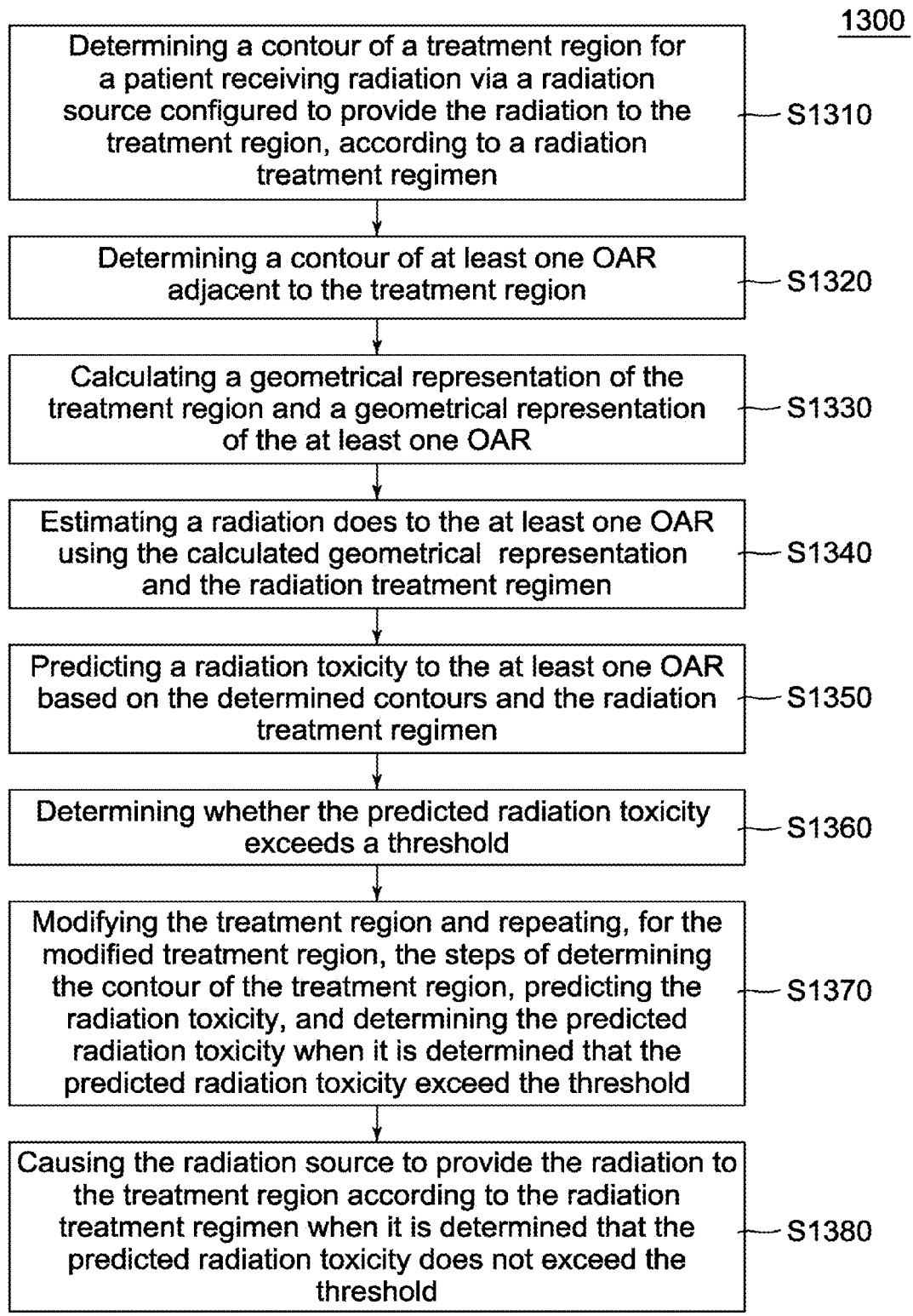
FIG. 13 is a flowchart illustrating a method of determining a radiation treatment region according to an embodiment.

FIG. 13 is a flowchart illustrating a method 1300, which includes determining a contour of a treatment region for a patient receiving radiation via a radiation source configured to provide the radiation to the treatment region according to a radiation treatment regimen in step S1310. The method 1300 also includes determining a contour of at least one OAR adjacent to the treatment region in step S1320, and calculating a geometrical representation of the treatment region and a geometrical representation of the at least one OAR in step S1330. The method 1300 also includes estimating a radiation dose to the at least one OAR using the calculated geometrical representation and the radiation treatment regimen in step S1330, estimating a radiation dose to the at least one OAR using the calculated geometrical representation and the radiation treatment regimen in step S1340, and predicting a radiation toxicity to the at least one OAR using the estimated radiation dose to the at least one OAR in step S1350. The method 1300 also includes determining whether the predicted radiation toxicity exceeds a threshold in step S1360. The method 1300 also includes modifying the contour of the treatment region and repeating, for the modified treatment region, the steps of determining the contour of the treatment region, predicting the radiation toxicity, and determining the predicted radiation toxicity when it is determined that the predicted radiation toxicity exceeds the threshold in step S1370, and causing the radiation source to provide the radiation to the treatment region according to the radiation treatment regimen when it is determined that the predicted radiation toxicity does not exceed the threshold in step S1380.

Method 1300 can also include retrieving estimated factors of radiation toxicity risk to the at least one OAR, uniformly expanding a contour of an identified organ of high toxicity risk, and detecting an overlapped region of the expanded contour of the identified organ of high toxicity risk and the treatment region. The overlapped region can be detected using an overlap volume histogram method.

Method 1300 can also include retrieving data for at least one prior patient having treatment factors similar to the patient, and determining a toxicity prediction model for the at least one prior patient using the treatment factors. In addition, method 1300 can include calculating a probability of toxicity for the patient using the determined toxicity prediction model, and identifying an organ of high toxicity risk using the determined toxicity prediction model. The retrieving step can include retrieving the data for the at least one prior patient using treatment factors, which include one or more of a geometrical representation of the treatment region and the at least one OAR, an estimated radiation dose to the at least one OAR, patient demographics, patient diagnoses, and patient assessment records. The toxicity prediction model can include determining the toxicity prediction model as one of a Nadaraya-Watson density estimation model and a decision-tree model and a logistic regression model.

Figure 14:
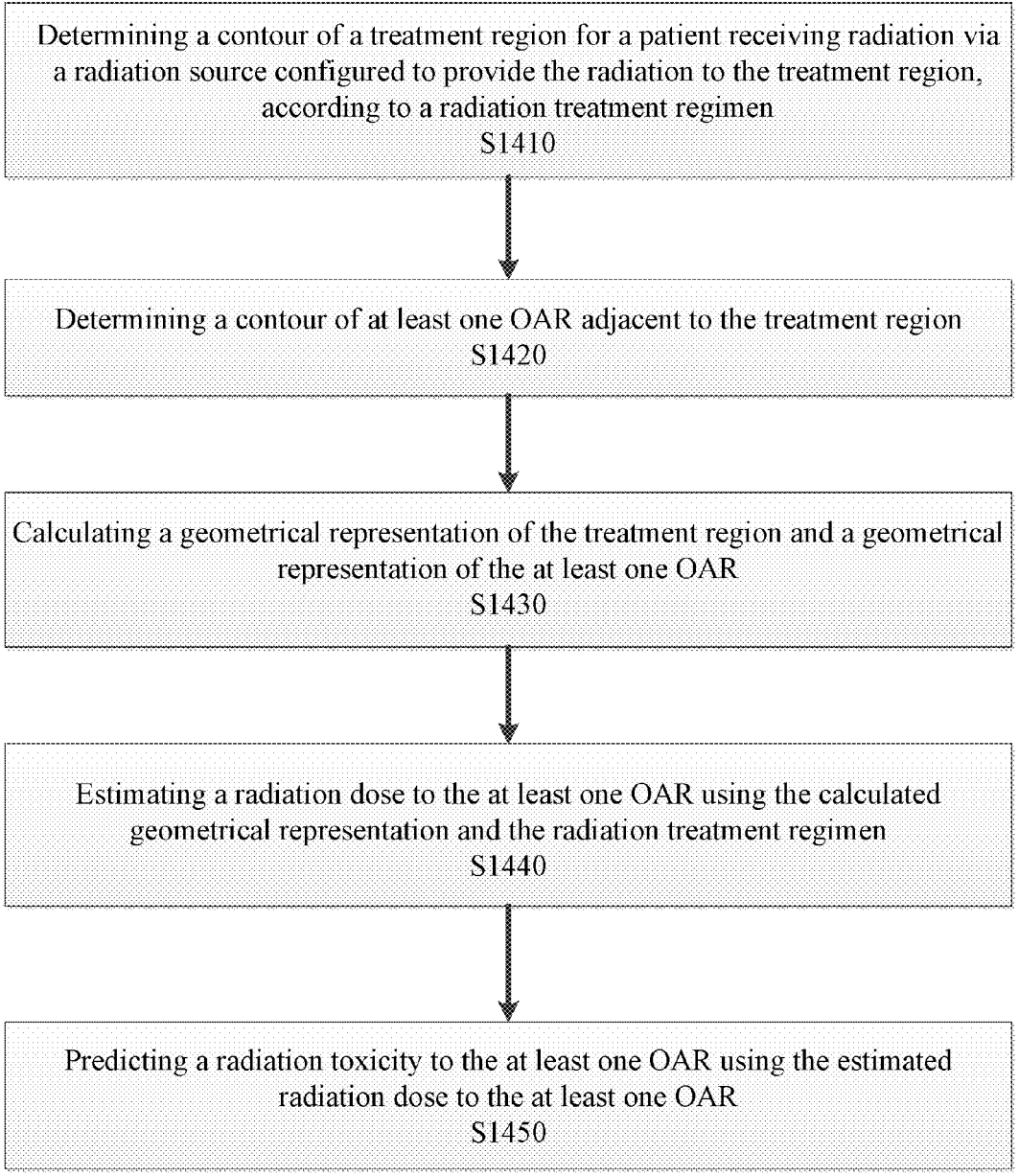
FIG. 14 is a flowchart illustrating a method of predicting radiation toxicity according to an embodiment.

FIG. 14 is a flowchart illustrating a method 1400 of predicting radiation toxicity. Method 1400 includes determining a contour of a treatment region for a patient receiving radiation via a radiation source configured to provide the radiation to the treatment region according to a radiation treatment regimen in step S1410. The method 1400 also includes determining a contour of at least one OAR adjacent to the treatment region in step S1420, and calculating a geometrical representation of the treatment region and a geometrical representation of the at least one OAR in step S1430. The method 1400 also includes estimating a radiation dose to the at least one OAR using the calculated geometrical representation and the radiation treatment regimen in step S1440, and predicting a radiation toxicity to the at least one OAR using the estimated radiation dose to the at least one OAR in step S1450.

Method 1400 can also include uniformly expanding the contour of the treatment region, and measuring an overlapped region of the uniformly expanded contour of the treatment region and the at least one OAR.

The foregoing discussion discloses and describes merely exemplary embodiments of the present disclosure. As will be understood by those skilled in the art, the present disclosure may be embodied in other specific forms without departing from the spirit or essential characteristics thereof. Accordingly, the present disclosure is intended to be illustrative, but not limiting of the scope of the disclosure, including the claims. The disclosure, including any readily discernible variants of the teachings herein, defines in part, the scope of the foregoing claim terminology such that no inventive subject matter is dedicated to the public.

The invention claimed is:

1. An apparatus, comprising:
  a computer processor configured to
    receive input regarding a contour of at least one organ-at-risk (OAR) adjacent to a treatment region in a patient;
    receive input regarding an initial contour of the treatment region;
    predict a radiation toxicity to the at least one OAR based on the contour of the at least one OAR, the initial contour of the treatment region, and a radiation treatment regimen;
    determine whether the predicted radiation toxicity exceeds a threshold; and
    determine a computer-generated contour of the treatment region by iteratively modifying said initial contour of the treatment region, and any subsequent modified contours of the treatment region, until a stopping condition is satisfied,
    wherein said stopping condition is at least one of a preselected number of iterations or that said predicted radiation toxicity using said computer-generated contour in place of said initial contour is first calculated to be below said threshold.

2. The apparatus of claim 1, wherein, to modify the contour of the treatment region, the computer processor is further configured to
  retrieve estimated factors of radiation toxicity risk to the at least one OAR,
  uniformly expand a contour of an identified organ of high toxicity risk, and
  detect an overlapped region of the uniformly expanded contour of the identified organ of high toxicity risk and the treatment region.

3. The apparatus of claim 2, wherein to modify the contour of the treatment region, the computer processor is further configured to
  expand the contour of the identified organ of high toxicity risk until a volume of the overlapped region reaches a specified volume,
  carve the overlapped region out of the treatment region, and
  update the contour of the treatment region.

4. The apparatus of claim 3, wherein to expand the contour of the identified organ of high toxicity risk until the volume of the overlapped region reaches a specified volume, the specified volume is equal to or less than a limit specified by a percentage of an original volume of the original treatment region determined by the initial contour of the treatment region.

5. The apparatus of claim 1, wherein, to predict the radiation toxicity to the at least one OAR, the computer processor is further configured to
  retrieve data for at least one prior patient having treatment factors similar to the patient,
  determine a toxicity prediction model for the at least one prior patient using the treatment factors,
  calculate a probability of toxicity for the patient using the determined toxicity prediction model, and
  identify an organ of high toxicity risk using the determined toxicity prediction model.

6. The apparatus of claim 5, wherein the computer processor is further configured to retrieve the data for the at least one prior patient using the treatment factors, which include at least one of a geometrical representation of the treatment region and the at least one OAR, an estimated radiation dose to the at least one OAR, patient demographics, patient diagnoses, and patient assessment records.

7. The apparatus of claim 5, wherein the computer processor is further configured to determine the toxicity prediction model as one of a Nadaraya-Watson density estimation model, a decision-tree model, and a logistic regression model.

8. The apparatus of claim 1, further comprising:
  a radiation source configured to provide radiation to the determined treatment region in the patient according to the radiation treatment regimen,
  wherein the computer processor is further configured to cause the radiation source to provide the radiation to the determined treatment region according to the radiation treatment regimen when it is determined that the predicted radiation toxicity does not exceed the threshold.

9. The apparatus of claim 1, further comprising a display to display the contour of the at least one organ-at-risk (OAR) and the determined contour of the treatment region.

10. The radiation treatment apparatus of claim 1, wherein the computer processor is further configured to calculate a geometrical representation of the treatment region by
  uniformly expanding the contour of the treatment region, and
  measuring an overlapped region of the uniformly expanded contour of the treatment region and the at least one OAR.

11. The radiation treatment apparatus of claim 10, wherein the computer processor is further configured to uniformly expand the contour of the treatment region using an overlap volume histogram method.

12. The radiation treatment apparatus of claim 1, wherein the computer processor is further configured to estimate a radiation dose to the at least one OAR by
- calculating a difference in distance between the treatment region and the at least one OAR for the patient and for at least one prior patient,
- identifying a prior patient of the at least one prior patient with a minimum difference in distance,
- retrieving treatment history data of the identified prior patient, and
- determining an estimated radiation dose to the at least one OAR for the patient based upon a previous radiation dose to the identified prior patient.

13. A method, comprising:
- receiving input regarding a contour of at least one organ-at-risk (OAR) adjacent to a treatment region in a patient;
- receiving input regarding an initial contour of the treatment region to receive radiation via a radiation source configured to provide the radiation to the treatment region, according to a radiation treatment regimen;
- predicting a radiation toxicity to the at least one OAR based on the contour of the at least one OAR, the initial contour of the treatment region, and a radiation treatment regimen;
- determining whether the predicted radiation toxicity exceeds a threshold; and
- determining a computer-generated contour of the treatment region by iteratively modifying said initial contour of the treatment region, and any subsequent modified contours of the treatment region, until a stopping condition is satisfied,
- wherein said stopping condition is at least one of a preselected number of iterations or that said predicted radiation toxicity using said computer-generated contour in place of said initial contour is first calculated to be below said threshold.

* * * * *